(12) United States Patent
Rade et al.

(10) Patent No.: US 12,005,257 B2
(45) Date of Patent: Jun. 11, 2024

(54) NEUROMODULATION THERAPY WITH CUSTOM INSTRUCTION SET ARCHITECTURE FOR A STIMULATION ENGINE SYSTEM

(71) Applicant: ADVANCED NEUROMODULATION SYSTEMS, INC., Plano, TX (US)

(72) Inventors: Gavin Rade, Dallas, TX (US); Daran DeShazo, Lewisville, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 17/405,804

(22) Filed: Aug. 18, 2021

(65) Prior Publication Data
US 2023/0066914 A1 Mar. 2, 2023

(51) Int. Cl.
| A61N 1/36 | (2006.01) |
| A61N 1/02 | (2006.01) |
| A61N 1/372 | (2006.01) |

(52) U.S. Cl.
CPC ......... *A61N 1/36167* (2013.01); *A61N 1/025* (2013.01); *A61N 1/36132* (2013.01); *A61N 1/37223* (2013.01); *A61N 1/37247* (2013.01)

(58) Field of Classification Search
None
See application file for complete search history.

(56) References Cited

U.S. PATENT DOCUMENTS

| 4,407,288 | A | * | 10/1983 | Langer | A61N 1/3925 607/4 |
| 5,464,435 | A | * | 11/1995 | Neumann | G06F 9/3879 607/9 |
| 7,024,246 | B2 | | 4/2006 | Acosta et al. | |
| 7,212,110 | B1 | | 5/2007 | Martin et al. | |
| 7,228,179 | B2 | | 6/2007 | Campen et al. | |
| 7,571,007 | B2 | | 8/2009 | Erickson et al. | |
| 9,844,661 | B2 | | 12/2017 | Franz et al. | |
| 10,391,322 | B2 | | 8/2019 | Griffith et al. | |
| 2006/0170486 | A1 | | 8/2006 | Tranchina et al. | |
| 2009/0048643 | A1 | | 2/2009 | Erickson et al. | |
| 2009/0326608 | A1 | | 12/2009 | Huynh et al. | |
| 2011/0072657 | A1 | | 3/2011 | Swanson et al. | |
| 2014/0343564 | A1 | | 11/2014 | Feler et al. | |
| 2018/0008821 | A1 | | 1/2018 | Gonzalez et al. | |
| 2020/0324120 | A1 | * | 10/2020 | Yu | A61N 1/36585 |
| 2021/0212901 | A1 | * | 7/2021 | Wood | G01P 15/00 |

FOREIGN PATENT DOCUMENTS

WO 2001093953 A1 12/2001

* cited by examiner

*Primary Examiner* — Erica S Lee
(74) *Attorney, Agent, or Firm* — Norton Rose Fulbright US LLP

(57) ABSTRACT

An implantable medical device (IMD) configured to provide stimulation therapy using an instruction set architecture (ISA) includes a main processor operating at a first frequency and a secondary processor operating at a second frequency lower than the first frequency. Example ISA may comprise assembly-language-like instructions that may be executed by the secondary processor for configuring one or more stimulation engines (SEs) to cause stimulation of select electrode sets of a lead system based on one or more pulse definitions and one or more timing definitions corresponding to a therapy program selection effectuated by a user at an external device.

7 Claims, 18 Drawing Sheets

| INSTRUCTION NAME | INSTRUCTION DESCRIPTION | REMARKS |
|---|---|---|
| SLP 1102 | WAIT FOR TIME SPECIFIED BY OFFSET | |
| LOAD 1104 | LOAD ENGINE WITH TYPE #XXXX | TYPE IS EITHER PULSE DEFINITION; TIMING DEFINITION; REQUIRES MEMORY ACCESS IF CACHE MISS |
| STORE 1106 | STORE TO MEMORY WITH ENGINE'S TYPE #XXXX | TYPE IS EITHER PULSE DEFINITION; TIMING DEFINITION |
| ALU 1108 | PERFORM ALU OPERATION ON ENG #ATTR | ALU OPs ARE ADD; SUB; SHFT LEFT; SHFT RIGHT; AND; OR; INVERT; XOR; IF ENG = 0xF, PERFORMS OPERATION ON A GLOBAL LEVEL |
| RPT 1110 | BRANCH UNTIL REPEAT COUNTER IS 0 | REPEAT COUNTER SET VIA SPECIAL ALU INSTRUCTION |

| 31 | 30 | 29 | 28 | 27 | 26 | 25 | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | 0 |
|---|---|---|---|---|---|---|---|---|---|---|---|---|---|---|---|---|---|---|---|---|---|---|---|---|---|---|---|---|---|---|---|
| OFFSET FROM GLOBAL TIMER (OVERFLOW AUTOMATICALLY TAKEN CARE OF) ||||||||||||||||||||||||||||| OPCODE ||||
| #XXXX ||||||||||||||||||||| TYPE ||||| ENG ||| OPCODE ||||
| #XXXX ||||||||||||||||||||| TYPE ||||| ENG ||| OPCODE ||||
| #VALUE ||||||||||||| ATTR ||||| ALU TYPE ||| ENG ||| OPCODE ||||
| UNUSED ||||||||||||||||||||||| # INSTR BACK ||||| OPCODE ||||

1122 → OFFSET FROM GLOBAL TIMER row
1124 → #XXXX row
1126 → #XXXX row
1128 → ATTR/#VALUE row
1130 → UNUSED row

| 31 | 30 | 29 | 28 | 27 | 26 | 25 | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | 0 |
|---|---|---|---|---|---|---|---|---|---|---|---|---|---|---|---|---|---|---|---|---|---|---|---|---|---|---|---|---|---|---|---|
| TIMING DEF ||||||| PULSE DEF ||||||||| AREA |||| ADC DATA ||||||||

1202 — TIMING DEF
1204 — PULSE DEF
1206 — AREA
1208 — ADC DATA

1200

NEUROMODULATION THERAPY WITH CUSTOM INSTRUCTION SET ARCHITECTURE FOR A STIMULATION ENGINE SYSTEM

TECHNICAL FIELD

The present disclosure generally relates to implantable medical devices (IMDs). More particularly, and not by way of any limitation, the present disclosure is directed to IMDs having an instruction set architecture for providing neuromodulation therapy using one or more stimulation engines.

BACKGROUND

Implantable medical devices have changed how medical care is provided to patients having a variety of chronic illnesses and disorders. For example, implantable cardiac devices improve cardiac function in patients with heart disease by improving quality of life and reducing mortality rates. Respective types of implantable neurostimulators provide a reduction in pain for chronic pain patients and reduce motor difficulties in patients with Parkinson's disease and other movement disorders. A variety of other medical devices are proposed and are in development to treat other disorders in a wide range of patients.

Stimulation systems often comprise a pulse generator coupled to one or more therapy delivery leads having a plurality of electrodes disposed in an area in which neurostimulation is desired. Alternatively, stimulation systems may comprise a micro-stimulation system in which a small implantable housing having electrodes thereon includes a pulse generator, wherein the entire micro-stimulation system is disposed in an area in which neurostimulation is desired. Depending on implementation, all or a portion of a stimulation system may not be implanted into a body to provide a desired therapy.

A stimulation system pulse generator may be provided in various configurations, such as a totally implanted pulse generator (IPG) or a radio frequency (RF)-based system. A typical IPG configuration comprises a surgically implanted, internally-powered pulse generator and one or more multi-electrode leads. A typical RF system configuration comprises a surgically implanted, passive receiver and a transmitter which is worn externally. In operation, the transmitter communicates, through an RF signal, to the implanted receiver to provide stimulation energy and control.

In a spinal cord stimulation (SCS) application, electrodes used with an example pulse generator, such as any of the foregoing pulse generators, deliver a particularized electric field to a specific region of the spinal cord or surrounding tissue. Applying such an electric field across one or more nerve bundles and/or nerve roots, if properly directed and produced at the necessary levels, can "mask" certain forms of chronic pain in a phenomenon referred to as "paresthesia". Applying low-amplitude stimulation parameters can also "mask" pain or other symptoms without producing "paresthesia" in some arrangements (e.g., a sub-paresthesia or non-paresthesia therapy system). Similarly, applying an electric field across other tissue, such as muscle or brain matter, near which such electrodes are disposed may provide a desired therapy. The focus, characteristics and intensity of the generated electric field are determined by the electrode configuration (the polarity, if any, assumed by each electrode) and the properties of an electric pulse waveform, which may generally include a stimulation frequency, a stimulation pulse width, a stimulation pulse amplitude, discharge method, and phase information, etc. (collectively "stimulation settings" or "stimsets").

Whereas advances in IPG systems and associated stimulation circuitry for use in various therapy applications continue to grow apace, several lacunae remain, thereby requiring further innovation as will be set forth hereinbelow.

SUMMARY

Embodiments of the present patent disclosure are broadly directed to neurostimulation systems and methods wherein an IPG, also referred to as an implantable medical device (IMD), may be configured to provide stimulation therapy to a patient using a customizable instruction set architecture (ISA). In one arrangement, the IPG may include a main processor operating at a first frequency and a secondary processor operating at a second frequency lower than the first frequency that is configured to control one or more stimulation engines (SEs) of the IPG/IMD. Example ISA may comprise assembly language instructions or similar low-level programming language instructions (e.g., a machine code set rendered in human-friendly mnemonics or syntax) provided by the main processor that may be executed by the secondary processor to configure one or more SEs for selectively stimulating respective electrode sets of a lead system based on one or more pulse definitions, one or more timing definitions, etc. corresponding to a therapy program selection effectuated by a user at an external device.

In one aspect, an embodiment of the present patent disclosure is directed to a method of operating an IMD for providing stimulation therapy to a patient, the IMD including one or more SEs operatively coupled to at least one implantable lead having a plurality of electrodes positioned proximate to a tissue of the patient. An example method comprises, inter alia, generating, by a first processor of the IMD operative with a first clock frequency, a set of pulse definitions and a set of timing definitions corresponding to a therapy program selection received from an external device responsive to a user input thereat and storing the respective sets of pulse definitions and timing definitions in a storage area. An example method may include generating, by the first processor, a sequence of assembly-language-like (ALL) instructions for execution by a second processor of the IMD operative with a second clock frequency that is lower than the first clock frequency, the second processor configured to control the one or more SEs for generating one or more pulse waveforms. An example method may include executing at least a portion of the ALL instructions by the second processor for causing the one or more SEs to generate a particular sequence of therapy pulses according to the therapy program selection based on respective combinations of the pulse definitions and timing definitions applied over a time base in accordance with the executed ALL instructions. In one arrangement, an example method may further include assembling a set of ALL instructions into executable program code and storing the executable program code in storage area for execution by the second processor without involving the first processor. In one arrangement, an example method may further include executing at least a portion of the ALL instructions by the second processor using an instruction pipeline architecture. In one arrangement, the time base employed in the execution of the ALL instructions may be derived from the second clock frequency of the second processor, the time base comprising a clock signal, wherein the example method may further include performing a verification at each clock edge of the clock signal to determine whether there are any pending instructions to be executed.

In another aspect, an embodiment of the present patent disclosure is directed to an IMD, which comprises, inter alia, one or more SEs operative to energize at least a portion of a plurality of electrodes of a lead system when implanted proximate to a tissue of a patient; and a first processor operative with a first clock frequency, the first processor configured to generate, responsive to a therapy program selection received from an external device, a set of pulse definitions, a set of timing definitions and a sequence of assembly-language-like (ALL) instructions corresponding to the therapy program selection. An example IMD may further include one or more persistent storage areas for storing the respective sets of pulse definitions and timing definitions, and executable program code assembled from the sequence of ALL instructions; and a second processor operative with a second clock frequency that is lower than the first clock frequency, the second processor configured to execute at least a portion of the executable program code corresponding to the ALL instructions for causing the one or more SEs to generate a particular sequence of therapy pulses according to the therapy program selection based on respective combinations of the pulse definitions and timing definitions applied over a time base in accordance with the executed ALL instructions. In one arrangement, the second processor of an example IMD may be configured to execute the executable program code using an instruction pipeline architecture. In one arrangement, the second processor of an example IMD may be configured to execute the executable program code without involving the first processor. In one arrangement, the time base employed in the execution of the ALL instructions may be derived from the second clock frequency of the second processor of the IMD, the time base comprising a clock signal, wherein the second processor may be configured to perform a verification at each clock edge of the clock signal to determine whether there are any pending instructions to be executed. In one arrangement, the example IMD may further include communication circuitry operative to effectuate a machine-to-machine (M2M) communication link with the external device using a wireless communication protocol for receiving the therapy program selection, wherein the external device may comprise a clinician programmer device operated by a clinician or a patient controller device operated by the patient.

Additional/alternative features, variations and/or advantages of the embodiments will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 11A and 11B depicts example ALL instructions and corresponding 32-bit machine code implementations according to an embodiment of the present patent disclosure;

FIG. 12 depicts an example 32-bit diagnostic data packet including pulse definition data, timing definition data, electrode area data and ADC data for purposes of an embodiment of the present patent disclosure;

DETAILED DESCRIPTION

Figure 1A:
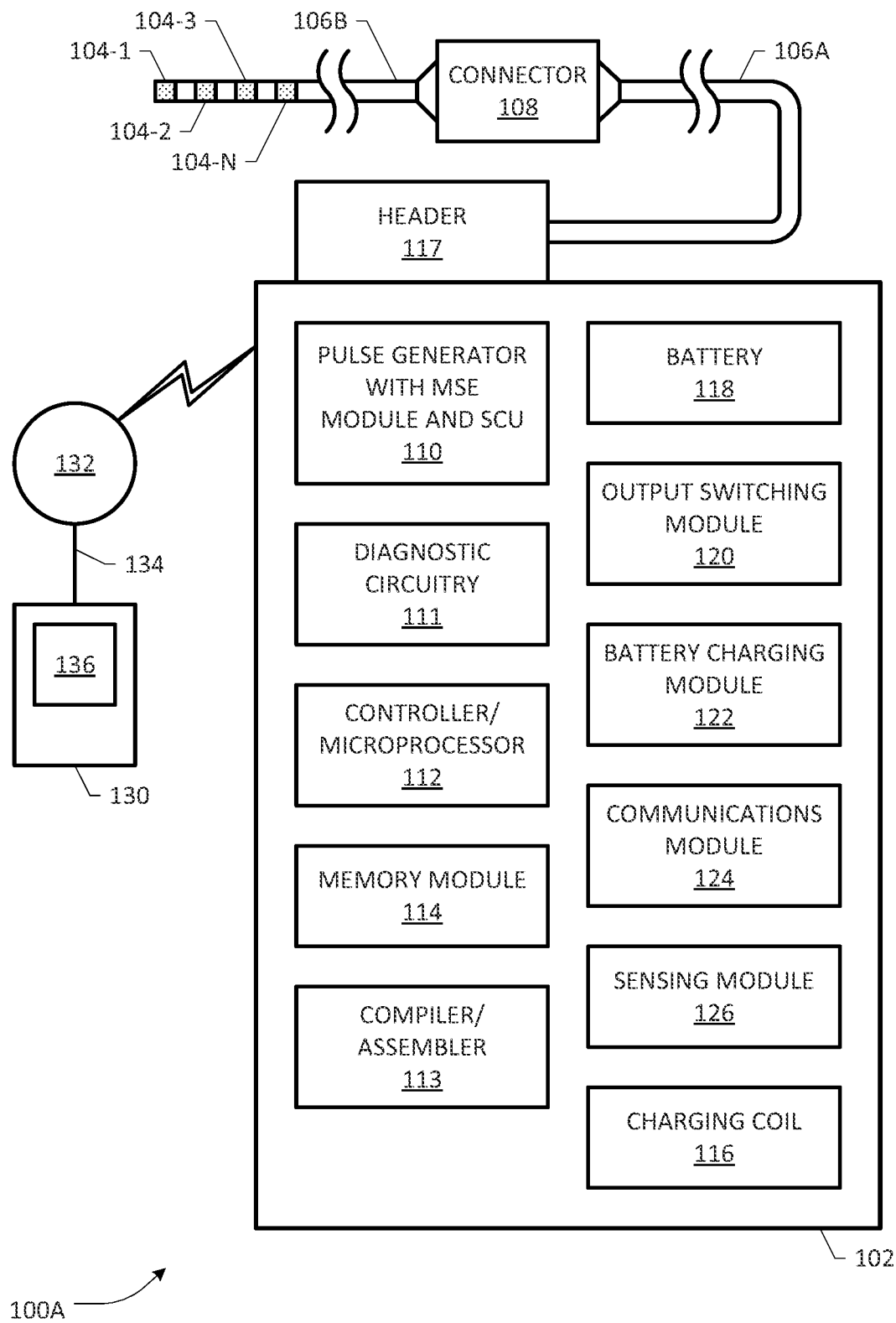
FIG. 1A depicts an example biostimulation system wherein an embodiment of an implantable medical device (IMD) having one or more stimulation engines (SEs) may be configured for providing stimulation therapy using a custom instruction set architecture (ISA) according to the teachings herein.

In the description herein for embodiments of the present disclosure, numerous specific details are provided, such as examples of circuits, devices, components, and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some embodiments described herein may be particularly set forth with respect to an implantable pulse generator (IPG) for generating electrical stimulation according to one or more multiple stimulation sets for application to a desired area of a body or tissue based on a suitable stimulation therapy application, such as a spinal cord stimulation (SCS) system. However, it should be understood that example circuitry and methods of operation disclosed herein are not limited thereto, but have broad applicability, including but not limited to different types of implantable devices such as neuromuscular stimulation systems and sensors, dorsal root ganglion (DRG) stimulation systems, deep brain stimulation systems, cochlear implants, retinal implants, implantable cardiac rhythm management devices, implantable cardioverter defibrillators, pacemakers, and the like, as well as implantable drug delivery/infusion systems, implantable devices configured to effectuate real-time measurement/monitoring of one or more physiological functions of a patient's body (i.e., patient physiometry), including various implantable biomedical sensors and sensing systems. Further, whereas some example embodiments of therapy applications may involve implantable devices, additional and/or alternative embodiments may involve external personal devices and/or noninvasive/minimally invasive (NIMI) devices, e.g., wearable biomedical devices, transcutaneous/subcutaneous devices, etc., that may be configured to provide therapy to the patients analogous to the implantable devices. Accordingly, all such devices may be broadly referred to as "personal medical devices," "personal biomedical instrumentation," or terms of similar import, at least for purposes of some example embodiments of the present disclosure.

Moreover, example circuitry and methods of operation disclosed herein are not limited to use with respect to an IPG or any particular form of IPG. For example, some embodiments may be implemented with respect to a fully implantable pulse generator, a radio frequency (RF) pulse generator, an external pulse generator, a micro-implantable pulse generator, inter alia.

Referring to FIG. 1A in particular, depicted therein is an example biostimulation system 100A wherein an embodiment of an implantable medical device (IMD) having one or more stimulation engines (SEs) may be configured for providing stimulation therapy using a custom instruction set architecture (ISA) according to the teachings herein. By way of illustration, system 100A may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as noted above. System 100A comprises an implantable pulse generator (IPG) or IMD 102 having a pulse generator portion 110 including one or more SEs operative to effectuate one or more stimulation therapies to the patient's tissue. In one arrangement, pulse generator portion 110 may include or be operatively associated with a global stimulation control unit (SCU) adapted to execute a plurality of assembly language or assembly-language-like (ALL) instructions (or, more generally, low-level instructions in a suitable syntax) provided according to a customizable architecture for controlling and configuring a select SE or a set of SEs in order to provide a therapy based on a therapy program selection as will be set forth in additional detail further below. In one example embodiment, IMD 102 may be implemented as having a metallic housing or can that encloses pulse generating circuitry module 110, a charging coil 116, a battery/power supply 118, a far-field and/or near field communication block or module 124, battery/power supply charging circuitry 122, output node switching circuitry 120, sensing circuitry 126, a main controller/processing block or module 112 operative with or to execute a compiler/assembler 113, e.g., in association with a memory module 114, and the like. Controller/processor module 112 may comprise a microcontroller or other suitable processor for controlling the various other components of IMD 102. In general, software/firmware code may be stored in memory 114, which may be integrated with the controller/processor module 112, and/or other suitable application-specific storage components (not particularly shown in this FIG.) for execution by microcontroller or processor 112 and/or other programmable logic blocks to provide the overall control of various components of IMD 102. Additionally, processor 112 may be configured as a primary or first processor operative in a first clock domain whereas an example SCU may be configured as a second/secondary processor (e.g., as a "co-processor") operative in a second clock domain that is based on a clock frequency lower than a clock frequency of the first clock domain for purposes of some embodiments of the present disclosure. Accordingly, appropriate oscillator circuit(s) may be provided with processor 112 and SCU (not specifically shown in this FIG.) for generating suitable clock signals used in the timing of the various operations of respective processor modules. As will be set forth in detail further below, processor 112 may be adapted to generate, e.g., under suitable program control, a set of pulse definitions and a set of timing definitions corresponding to a therapy program selection received from an external device, e.g., device 130, responsive to a user input thereat. Further, processor 112 may be adapted to generate a sequence or set of ALL instructions for execution by the SCU operating as the secondary processor in order to control and configure one or more SEs for generating one or more pulse waveforms pursuant to the therapy program selection. In one arrangement, the respective sets of pulse definitions, timing definitions as well as assembled ALL instructions may be stored in respective portions of a persistent storage area that may be organized as part of memory 114 and/or in association with a distributed storage space managed by a memory management unit wherein the storage space may be physically, logically and/or virtually organized and/or partitioned into units that may be co-located with various components of IMD 102, e.g., processor 112, SCU/pulse generator module 110, memory 114, and the like.

In one arrangement, IMD 102 may be coupled to a separate or an attached extension component 106A for providing electrical and physical connectivity to a lead system via a lead connector 108, wherein one or more leads each having a respective plurality of electrodes may be provided. By way of example, a single lead 106B is illustrated, wherein a distal end of the single lead 106B includes a plurality of electrodes 104-1 to 104-N, which in one embodiment may respectively correspond to a plurality of output nodes driven by output switching module 120 in association with pulse generator portion 110. Extension component 106A may connect with a header 117 of IPG/IMD 102 as is known in the art. If the extension component 106A is integrated with IMD 102, internal electrical connections may be made through respective conductive components. In general operation, electrical pulses are generated by one or more SEs of the pulse generating circuitry 110 under the control of SCU's execution of ALL instruction set, and are provided to the output switching circuitry 120 that is operative to selectively connect to electrical outputs of the IMD (i.e., output nodes), which are ultimately coupled to electrodes 104-1 to 104-N at a distal end of the lead system 106B via respective electrical conductive traces.

In one arrangement, lead electrodes 104-1 to 104-N may be positioned along an axis of the lead 1066, with an angular offset such that the lead electrodes 104-1 to 104-N do not overlap. The lead electrodes 104-1 to 104-N may be in the shape of a ring such that each lead electrode continuously covers the circumference of the exterior surface of the lead 106B (e.g., deployed as a percutaneous lead). Each of the lead electrodes 104-1 to 104-N are separated by non-conducting portions of the lead 106B, which electrically isolate each lead electrode 104-1 to 104-N from an adjacent lead electrode 104-1 to 104-N. The non-conducting portions of the lead 106B may comprise one or more insulative materials and/or biocompatible materials to allow the lead 106B to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane, or the like compositions.

Additionally or alternatively, electrodes 104-1 to 104-N may be in the shape of a split or non-continuous ring such that the stimulation pulse(s) may be emitted in a manner so as to create an electric field emanating in an outward radial direction adjacent to the lead electrodes 104-1 to 104-N. Examples of lead electrodes 104-1 to 104-N and associated fabrication processes are disclosed in one or more of the following: (i) U.S. Patent Application Publication No. 2011/0072657, entitled, "METHOD OF FABRICATING STIMULATION LEAD FOR APPLYING ELECTRICAL STIMULATION TO TISSUE OF A PATIENT"; and (ii) U.S. Patent Application Publication No. 2018/0008821, entitled, "IMPLANTABLE THIN FILM DEVICES", each of which is incorporated herein by reference. Further, it should be noted the lead electrodes 104-1 to 104-N may be in various other formations, for example, in a planar formation, in an array or grid, etc. on a paddle structure as disclosed in U.S. Patent Application Publication No. 2014/0343564, entitled, "PADDLE LEADS FOR NEUROSTIMULATION AND METHOD OF DELIVERYING THE SAME", which is incorporated herein by reference.

In one arrangement, lead system 106B (including extension 106A where provided) may comprise a lead body of insulative material encapsulating a plurality of conductors within the material that extend from a proximal end (that is proximate to IMD 102) to the distal end of the lead body containing electrodes 104-1 to 104-N. The conductors or conductive traces are operative to electrically couple electrodes 104-1 to 104-N to a corresponding plurality of terminals (not shown) of the lead system 106A/B. In general, the terminals are adapted to receive electrical pulses from the pulse generation and switching circuitry of IMD 102 via a set of output nodes driven by the output switching circuitry 120, which are propagated by the corresponding conductive traces to at least a corresponding portion of electrodes 104-1 to 104-N that are adapted to apply the pulses to a desired stimulation target of the patient depending on the particular stimulation therapy application. Also, sensing of physiological or bioelectrical signals may occur in some embodiments through lead electrodes 104-1 to 104-N, corresponding conductors, and associated terminals. By way of further illustration, an example embodiment of the stimulation system 100A may be provided with one or more leads, each having a plurality of lead electrodes 104-1 to 104-N comprising four electrodes, eight electrodes, etc., although any suitable number of electrodes (as well as corresponding conductive traces and terminals) may be provided, wherein the leads may be configured to be positioned proximate to a patient's tissue at one or more locations for providing appropriate stimulation therapy/therapies by activating/deactivating suitable output switching portions after implant. Additionally, alternatively, or optionally, various sensors (e.g., a position detector, temperature sensor, one or more electrochemical sensors, a radiopaque fiducial, etc.) may be located near the distal end of the lead 106B and electrically coupled to terminals through associated conductors within the lead body.

Although not required for all embodiments, the lead body of the implantable lead system 106A/106B may be fabricated to flex and elongate upon implantation or advancing within or relative to the tissue (e.g., nervous tissue) of the patient towards the stimulation target to account for movement of the patient during or after implantation. Fabrication techniques and material characteristics for "body compliant" leads are disclosed in greater detail in U.S. Pat. No. 9,844,661, entitled "COMPLIANT ELECTRICAL STIMULATION LEADS AND METHODS OF FABRICATION", which is incorporated herein by reference.

An example implementation of the components within IMD 102, such as, e.g., processor and associated charge control circuitry for pulse generation, is described in U.S. Pat. No. 7,571,007, entitled "SYSTEMS AND METHODS FOR USE IN PULSE GENERATION", incorporated herein by reference, which may be adapted for controlling and/or for operating in association with a secondary processor configured as an SCU for purposes of an embodiment of the present patent disclosure. An example implementation of circuitry for recharging a rechargeable battery (e.g., battery charging circuitry 122) of an IMD using inductive coupling and external charging circuits is described in U.S. Pat. No. 7,212,110, entitled "IMPLANTABLE DEVICE AND SYSTEM FOR WIRELESS COMMUNICATION", which is incorporated herein by reference. Still further, an example implementation of "constant current" pulse generating circuitry (e.g., operative as at least a portion of pulse generating circuitry 110) is provided in U.S. Patent Application Publication No. 2006/0170486 entitled "PULSE GENERATOR HAVING AN EFFICIENT FRACTIONAL VOLTAGE CONVERTER AND METHOD OF USE", incorporated herein by reference, which may be adapted for controlling and/or for operating in association with a secondary processor configured as an SCU for purposes of an embodiment of the present patent disclosure. In some example embodiments, one or multiple sets of such circuitry may be provided for operation in association with respective current regulation circuitry as part of individual stimulation engines of module 110 for independently energizing different portions or sets of the electrodes of the lead system. In some example embodiments, different stimulation pulses on different lead electrodes selected from electrodes 104-1 to 104-N may be generated according to a "multi-stimset program" as is known in the art. Complex pulse parameters may be employed such as those described in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated herein by reference. Additionally, alternatively and/or optionally, multiple sets of such stimulation circuitry may be employed to provide different types of pulse patterns (e.g., tonic stimulation waveform patterns, burst stimulation waveforms, high-frequency stimulation waveform patterns, and the like) that may include selective stimulation therapy treatments through one or more leads or electrodes 104-1 to 104-N, wherein some of the some of the treatments may comprise non-paresthesia/sub-paresthesia stimulation therapies. Various sets of parameters may define the pulse characteristics and pulse timing for the pulses applied to the various lead electrodes, which may be defined and applied in accordance with a custom ISA executed by the SCU as will be set forth further below. It should be appreciated that although constant current pulse generating circuitry is contemplated with respect to some embodiments, any other suitable type of pulse generating circuitry may be employed in association with the SE arrangement activated under the control of the secondary processor for purposes of some embodiments of the present disclosure.

In an example implementation of IMD 102, sensing circuitry 126 may be optionally provided, preferably adapted to measure a suitable electric parameter or transduced characteristic (e.g., voltage, current, capacitance, etc.) over a configurable or select time associated with the stimulation target or tissue through at least one of the electrodes proximate to the stimulation target. For example, an implementation of sensing circuitry 126 may measure an evoked compound activation potential (ECAP) waveform from an Aβ sensory fiber or spinal cord. Optionally, sensing circuitry 126 may store the measured/sensed electric data in memory 114. Furthermore, diagnostic circuitry 111 may be configured to interoperate with sensing circuitry 126 and pulse generation and switching functionalities effectuated by SCU module 110 of IMD 102 for generating suitable diagnostic control signals that may be configured to adjustably control the operation of a multi-SE arrangement for purposes of some example embodiments of the present patent disclosure.

In some arrangements of system 100A, external device 130 may be implemented to charge/recharge the battery/power supply 118 of IMD 102 (although a separate recharging device could alternatively be employed), to access memory 114, and/or to program or reprogram IMD 102 with respect to a select therapy program, e.g., based on a set or sets of stimulation parameters including pulsing/timing specifications, while implanted within the patient. In alternative embodiments, however, separate programmer devices may be employed for charging and/or programming IMD 102 device and/or any programmable components thereof. An example embodiment of the external device 130 may be a processor-based system having wireline and/or wireless communication capabilities, which may comprise commercial off-the-shelf (COTS) equipment such as a portable computer, smartphone, tablet, phablet, laptop, handheld computer, a personal digital assistant (PDA), or any smart wearable device and smart digital assistant device, or the like, or any proprietary portable medical/healthcare device (i.e., non-COTS device), that may be configured to execute a therapy application program or other type of software, generally referred to as an "app", that may be invoked via a suitable user interface, e.g., a graphic UI (GUI), a voice-based UI, etc., wherein various types of communications relating to mode selection control, therapy/diagnostics, and/or test program and stimulation therapy program management and selection may be effectuated with respect to IMD 102. Additional or related software may be stored within a non-transitory memory of external device 130, which may be executed by the processor to control the various operations of the external device 130. In some arrangements, a connector or "wand" 134 may be electrically coupled to the external device 130 through suitable electrical connectors (not specifically shown), which may be electrically connected to a telemetry component 132 (e.g., inductor coil, RF transceiver, etc.) at the distal end of wand 134 through respective communication links that allow bi-directional communication with IMD 102. Alternatively, there may be no separate or additional external communication/telemetry components provided with external device 130 in an example embodiment for facilitating bi-directional communications with IMD 102 (e.g., based on Bluetooth Low Energy or BLE, and the like).

In some arrangements, a user (e.g., a doctor, a medical technician, or the patient, or a respective authorized agent) may initiate communication with IMD 102 by placing the wand 134 proximate to the patient. Preferably, where implemented, the placement of the wand 134 allows the telemetry system to be aligned with the far-field and/or near field communication circuitry 124 of IMD 102. External device 130 preferably provides one or more user interfaces 136 (e.g., touch screen, keyboard, mouse, buttons, scroll wheels or rollers, or the like, as well as audio/visual (AV) interfaces), allowing the user to operate IMD 102. External device 130 may be controlled by the user through user interface 136, allowing the user to interact with IMD 102, including, e.g., effectuating programmatic control for dynamically configuring stimulation current pulses as well as independent selection/activation of different stimulation engines in some embodiments. Further, user interface 136 may permit the user to move electrical stimulation along and/or across one or more of the lead(s) 106A/B using different lead electrode combinations selected from electrodes 104-1 to 104-N, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME", which is incorporated herein by reference. Optionally, user interface 136 may permit the user to designate which sets or subsets of electrodes 104-1 to 104-N are to stimulate (e.g., emit current pulses, in an anode state, in a cathode state), or not selected to stimulate (i.e., remain inactive or floating), with respect to a potential stimulation target, to measure/sense tissue electrical parameters, or the like. Additionally, some electrodes of the lead system 106/NB may be configured to operate as current sink terminals or cathodes whereas other electrodes may be configured as current source terminals or anodes. Additionally or alternatively, external device 130 may access or download the electrical measurements from memory 114 acquired by example sensing/diagnostics circuitry modules 126/111, which may be utilized by the user in selecting a different therapy program and/or otherwise (re)adjust a selected therapy program for causing a revised/adjusted set of custom instructions to be generated or obtained that may be executed by the SCU for purposes of some embodiments herein.

In some embodiments, external device 130 may be used in a test mode for testing an IMD over a trial period before permanently implanting in a patient. Regardless of whether the IMD is being operated in a test mode or in a permanent implant mode, medical application software (e.g., including software as a medical device (SaMD)), executing on external device 130 may be configured to permit operation of IMD 102 according to one or more stimulation therapy programs or applications (e.g., an SCS application, a DRG application, a DBS application, etc.) to treat the patient. Depending on application, a therapy program may be based on or otherwise include one or more sets of stimulation parameters of a pulse train wherein the pulses may be defined according to respective parameters such as, e.g., pulse amplitude, stimulation level, pulse width, pulse frequency or inter-pulse period, pulse repetition parameter (e.g., number of times for a given pulse to be repeated for respective stimulation sets or stimsets during execution of program), biphasic pulsing, monophasic pulsing, etc. IMD 102 may be configured to modify its internal parameters in response to a therapy selection signal emanating from external device 130 based on the execution of a custom set of ALL instructions, wherein pulse waveform characteristics of the respective stimulation therapies may be delivered by the multiple stimulation engines and transmitted through the selected portions of the electrodes of lead system 106A/106B to the tissue of the patient. Example stimsets and multi-stimset programs that may be modified and/or used for operation in association with one or more stimulation engines under programmatic control of a combination of primary and secondary processors for purposes of the present patent disclosure may be found in U.S. Pat. No. 7,228,179, entitled "METHOD AND APPARATUS FOR PROVIDING COMPLEX TISSUE STIMULATION PATTERNS", and International Patent Publication Number WO 2001/093953, entitled "NEUROMODULATION THERAPY SYSTEM", which are incorporated hereinabove by reference.

Figure 1B:
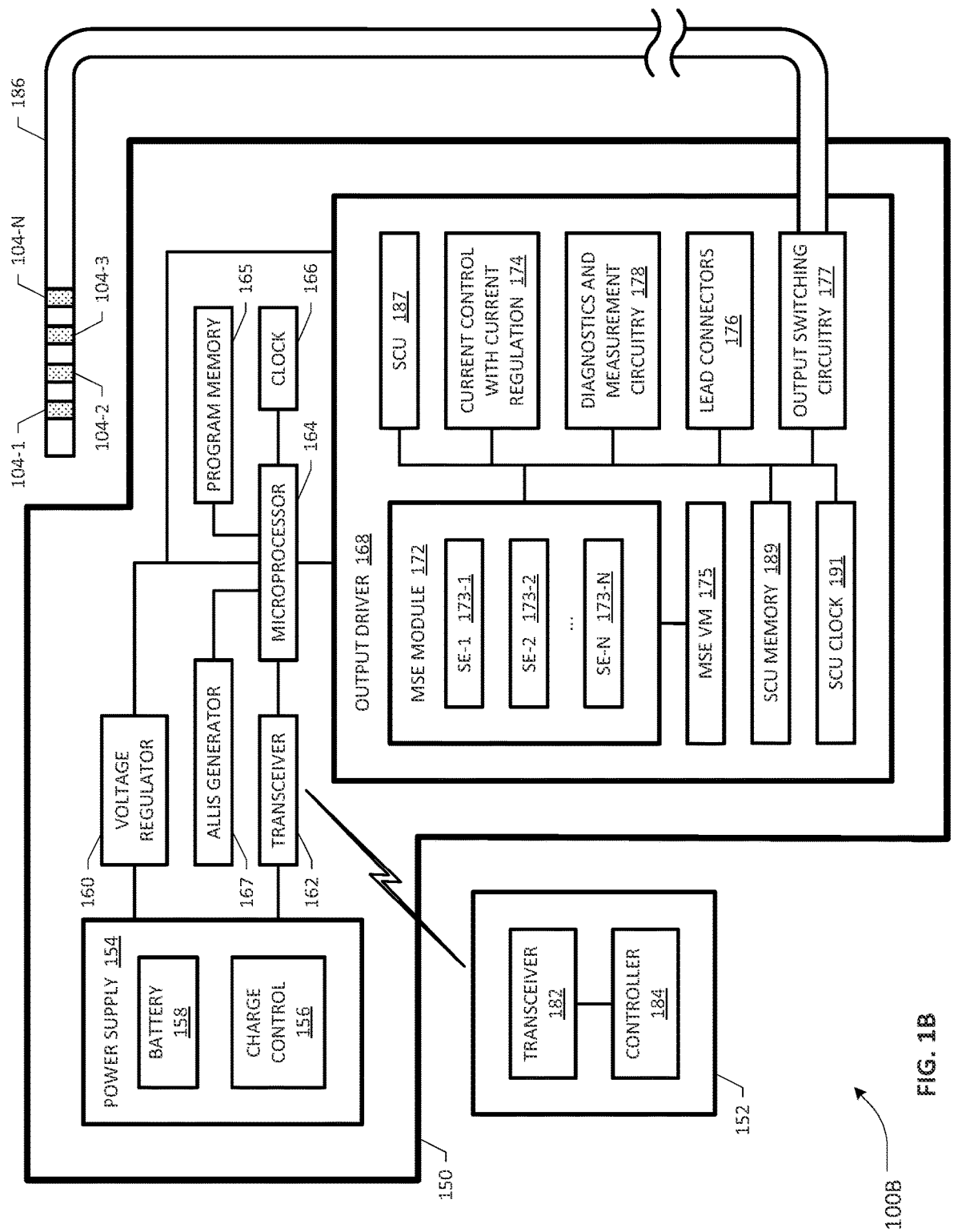
FIG. 1B depicts another view of a biostimulation system that illustrates additional details of an IMD's pulse generator including a second processor operative with an assembly-language-like (All) instruction set (ALLIS) facilitated by a main processor of the IMD for providing stimulation therapy according to an embodiment of the present patent disclosure.

FIG. 1B depicts another view of a biostimulation system that illustrates additional details of an IMD's pulse generator including a second processor operative with a custom ALL instruction set (ALLIS) facilitated by a main processor of the IMD for providing stimulation therapy according to an embodiment of the present patent disclosure. Stimulation system 100B is adapted to include a generator portion, shown as IPG 150, providing a stimulation or energy source, a stimulation portion, shown as lead system 186 for application of the stimulus pulse(s) similar to the lead system 106A/B described above, and an optional external controller, shown as programmer/controller 152, to program and/or control IPG 150 via a wired/wireless communications link, similar to external device 130 described in the foregoing sections. IPG 150 may be implanted within the body of a human or animal patient (not shown) for providing electrical stimulation from IPG 150 to a selected area of the body via lead 186 under control of external programmer/controller 152. It should be appreciated that although lead 186 is illustrated to provide a stimulation portion of stimulation system 100B configured to provide stimulation remotely with respect to the generator portion 150 of stimulation system 100B, a lead as described herein is intended to encompass a variety of stimulation portion configurations including, e.g., a microstimulator electrode disposed adjacent to a generator portion.

Furthermore, although example lead systems 186 and 106A/B shown in FIGS. 1A/1B are exemplified as a single implantable lead, the teachings herein are not necessarily limited thereto. An example embodiment of the present disclosure may involve a lead system comprising two or more implantable leads, with each lead having a respective plurality of electrodes, wherein different combinations of electrodes/leads may be grouped into one or more channels in a stimulation therapy system. Regardless of whether one or more leads and/or one or more sets of electrodes are selected for stimulation, therapy pulses according to a select one or more therapies may be applied by respective stimulation engines to different portions of electrodes according to a particular channel selection scheme that may be effectuated by a particular set of custom ALL instruction set according to some embodiments set forth herein.

IPG 150 may be configured as a self-contained implantable pulse generator having an implanted power source such as a long-lasting or rechargeable battery. Alternatively, IPG 150 may comprise an externally-powered implantable pulse generator receiving at least some of the required operating power from an external power transmitter, preferably in the form of a wireless signal, which may be radio frequency (RF)-based, via inductive coupling, etc., as noted previously. IPG 150 of the illustrated embodiment includes a voltage regulator 160, power supply 154, transceiver 162, main processor such as a microcontroller (or microprocessor) 164 operative with a main/primary clock 166 in a first clock domain, and output driver circuitry 168 for generating pulse waveforms under programmatic control executed in a second clock domain. In one arrangement, driver circuitry or module 168 may comprise a stimulation engine (SE) module 172 having one or more stimulation engines (SEs) 173-1 to 173-N, each having respective current regulation circuitry, switchable connectivity to a voltage multiplier (e.g., VM 175) as well as output switching circuitry 176 for switchably connecting output nodes to lead system 186, wherein a secondary processor 187 operating in the second clock domain based on a secondary clock 191 may be provided for controlling and configuring the SEs under programmatic control as will be described in further detail below. In some arrangements, optionally, alternatively and/or additionally, a local memory or storage space 189 as well as a separate current control/regulation block 174 along with a switchable voltage multiplier may be provided for operation with SE module 172 and/or SCU 187. Further, suitable diagnostic circuitry 178 may also be provided as part of output driver 168 in some embodiments.

Power supply 154 provides a source of power, such as from battery 158 (which may comprise a non-rechargeable battery, e.g., single use battery, a rechargeable battery, a capacitor, and/or like power sources), to other components of IPG 150, as may be regulated by voltage regulator 160 including and/or facilitating digitally-programmable analog voltage generation. Charge control 156 of an example embodiment of IPG 150 is operative to provide recharging management with respect to battery 158. Transceiver 162 of an example embodiment of IPG 150 is operative to provide data/control communication between main microprocessor 164 and a controller 184 of external programmer/controller 152, via transceiver 182 provided therewith. Transceiver 162 of an example embodiment, in addition to or in the alternative to providing data/control communication, may provide a conduit for delivering energy to power supply 158 via RF or inductive recharging as previously noted.

In one arrangement, main processor/controller 164 (which may be referred to using various acronyms, abbreviations, or initialisms, such as, e.g., MPU, MCU or similar terms) may be configured to provide overall control with respect to the operation of IPG 150, such as in accordance with one or more programs or code portions stored therein (e.g., in memory 165) or provided thereto by way of a selection from external programmer/controller 152. Further, program code or software may be provided in some embodiments wherein main processor 164 may be configured to generate, upon executing the program code responsive to a therapy program selection received from external device 152, a sequence of ALL instructions corresponding to the therapy program selection wherein the ALL instructions are specific to and/or adapted for the architecture of the SCU depending on implementation. Such code may be stored in memory 165 or in a separate storage area operative as an executable module, e.g., as ALLIS generator or compiler 167. Still further, program code or software may be provided in some embodiments wherein MCU 164 may be configured to generate, upon executing the program code responsive to the therapy program selection received from external device 152, various sets of pulse definitions and timing definitions relating to the selected therapy program. Furthermore, depending on implementation, the custom ALL instructions may be compiled or assembled by an assembler/compiler into executable machine code for execution by a secondary processor such as SCU 187.

In general, MCU 164 and SCU 187 may be implemented using any known or heretofore unknown processor technologies and computing architectures operating at or with different clock speeds, address and data bus widths, etc. In some embodiments, MCU 164 and SCU 187 may comprise processors from a class of reduced instruction set computing (RISC) architectures such as Advanced RISC Machines (ARM) including ARM cores (e.g., 32-bit cores, 64-bit cores, etc.) that may be provided as part of system-on-chip (SoC) or system-on-module (SoM) devices, although other architectures such as complex-instruction set computing (CISC) architectures may also be used in alternative or additional arrangements. Still further, processing functionalities of MCU 164 and/or SCU 187 may be implemented using intellectual property (IP) cores integrated into ASICs or FPGAs etc. in some embodiments. Regardless of a particular architectural arrangement, embodiments herein may include an MCU running at faster clock frequencies (e.g., in a range of several megahertz to gigahertz or thereabouts) and higher operating currents (e.g., in several microamps or thereabouts) whereas a slower SCU running at frequencies in a range of 100 kHz that consumes less power (i.e., using lower operating currents of 50-125 nanoamps or thereabouts) may be provided for executing ALLIS-based stimulation instructions.

Depending on implementation, at least a portion of the following parameters or stimulation information may be provided that may be acted upon during the execution of one or more ALLIS-based stimulation instructions for purposes of some embodiments of the present patent disclosure. A pulse attribute may be defined as a property of a single stimulation pulse such as, e.g., pulse width, amplitude, time to next pulse, etc. A pulse definition may be configured as a collection of pulse attributes which when run by a stimulation engine are operative to output a pulse waveform. In one arrangement, a pulse definition may comprise variable and/or selectable sequence of attributes, which may be dynamically created or preconfigured. A timing definition may be configured as a collection of timing information used by an SE in outputting a pulse waveform. As will be seen further below, each SE may be provided with a suitable set of registers that may be used for storing one or more attributes and pulse/timing definitions that are caused to be moved from an external storage area in response to programmatic control provided pursuant to the execution of assembled ALLIS stimulation instruction code. Still further, example embodiments herein provide an architecture that facilitates the transportation of pulse attributes, pulse definitions, timing definitions, etc., (cumulatively referred to as "stimulation data") from one storage area of the IMD (e.g., referred to as "external" or "nonlocal" memory space) to one or more registers of a select SE or SEs without requiring the intervention of a main processor because of the involvement of a secondary processing entity for executing such operations.

Skilled artisans will recognize that the various portions of storage areas used for storing machine-executable ALLIS-based stimulation instructions as well as stimulation data may be organized in any known or heretofore unknown computer memory technologies, architectures and memory management techniques, etc, wherein different storage areas may be associated with and/or partitioned between the processing units, physically, logically, and/or virtually. In some embodiments, a memory management unit may be provided to manage virtual memory address spacing, memory protection/buffering, cache control, bus arbitration, etc., with respect to storing the data and/or instructions. Regardless of a particular processor/memory architectural implementation, it should be appreciated that by providing a simple yet customizable assembly-like instruction set for executing stimulation instructions that does not require the involvement of a main MCU of the IMD, example embodiments herein may be configured to provide increased flexibility while simultaneously affording low power control of multiple SEs in an exemplary therapy system.

Output of SCU 187 may be utilized in configuring a select one or more SEs 173-1 to 173-N of MSE module 172 to generate and deliver stimulation therapies having suitable pulse characteristics to selected sets or portions of electrodes 104-1 to 104-N. In one embodiment, for example, different SEs 173-1 to 173-N of MSE module 172 may be controlled to output optimized stimulation therapies simultaneously without collisions to different sets of electrodes selected under programmatic control. By way of illustration, a stimulation therapy may comprise delivering a constant current pulse of a desired magnitude/amplitude, duration, phase, and frequency to a tissue load present with respect to particular ones/sets of electrodes 104-1 to 104-N, which may be represented as respective lumped-element electrode/tissue interface (ETI) loads. In one arrangement, a time base provided by SCU clock 191 may be operative to supply stimulation timing information as well as timing signals for controlling and coordinating different portions of MSE module 172 and/or VM 175 in generating desired voltages, controlling switchable connectivity to VM 175, etc., described below in further detail with respect to an example embodiment.

In one arrangement, voltage regulator 160 may be configured to accept a reference voltage $V_{REF}$, which may be prone to variation in magnitude, and provide an output voltage $V_{OUT}$ having a selected, relatively constant magnitude. For example, $V_{REF}$ may be provided by battery 158 which may have a relatively high voltage when initially charged or put into service and the voltage may drop over the life or charge cycle of the battery. However, circuitry of IPG 150 may malfunction if a voltage applied thereto is not within particular limits, and the high and low voltage extremes associated with battery 158 may be outside of these limits in some instances. Accordingly, voltage regulator 160 may be configured to provide a regulated supply $V_{OUT}$ within a range acceptable to circuitry of IPG 150, including output driver circuitry 168 having MSE module 172, associated voltage multiplier 175 and SCU-driven global engine control for purposes of an example embodiment of the present disclosure.

In general operation, a typical voltage regulator is capable of maintaining an output voltage only when the reference voltage provided thereto is at least slightly higher than the output voltage. However, over the course of a battery's life or charge cycle, the voltage provided thereby may be reduced to a point too close to or below the $V_{OUT}$, causing the voltage regulator output voltage to also fall. In such a situation, therefore, the regulator can no longer provide the desired regulated output voltage. However, voltage regulator 160 of an embodiment may be adapted to provide a desired output voltage level even when a reference voltage provided by battery 158 drops below the desired output voltage.

In one example implementation, voltage regulator 160 may include a multiplexer having multiple voltage inputs that are at different levels of the battery voltage ($V_B$), which may be selected under programmatic control to provide a suitable voltage supply output for the components of IPG 150. Some embodiments may also implement a closed loop control system with respect to voltage regulator 160 in order to provide further voltage selection control in association with suitable control signaling. For example, sensing circuitry, such as may utilize an analog-to-digital converter (ADC) in making voltage measurements may be utilized according to an example embodiment to provide information with respect to the battery voltage, which may be used by a digital control system (e.g., supported by MCU/MPU 164) in order to provide appropriate control signals for controlling the output voltage of voltage regulator 160. Additional details regarding voltage regulation, which may be adapted to supply appropriate voltage levels for SEs 173-1 to 173-N controlled by SCU 187, may be found in U.S. Patent Application Publication No. 2009/0048643, entitled "METHOD FOR PROVIDING MULTIPLE VOLTAGE LEVELS DURING PULSE GENERATION AND IMPLANTABLE PULSE GENERATING EMPLOYING THE SAME" (hereinafter "the '643 patent application publication"), hereby incorporated herein by reference.

Skilled artisans will recognize that although an embodiment of voltage regulation is set forth hereinabove, a variety of techniques and circuits may be provided for operation with an IPG having multiple SEs described below in a particular implementation. Generally, any suitable voltage regulator/multiplier arrangement may be adapted to provide a dynamic voltage adjustment to cover the voltage levels required for different stimulation currents under different loads according to some example embodiments of the present disclosure.

Figure 2:
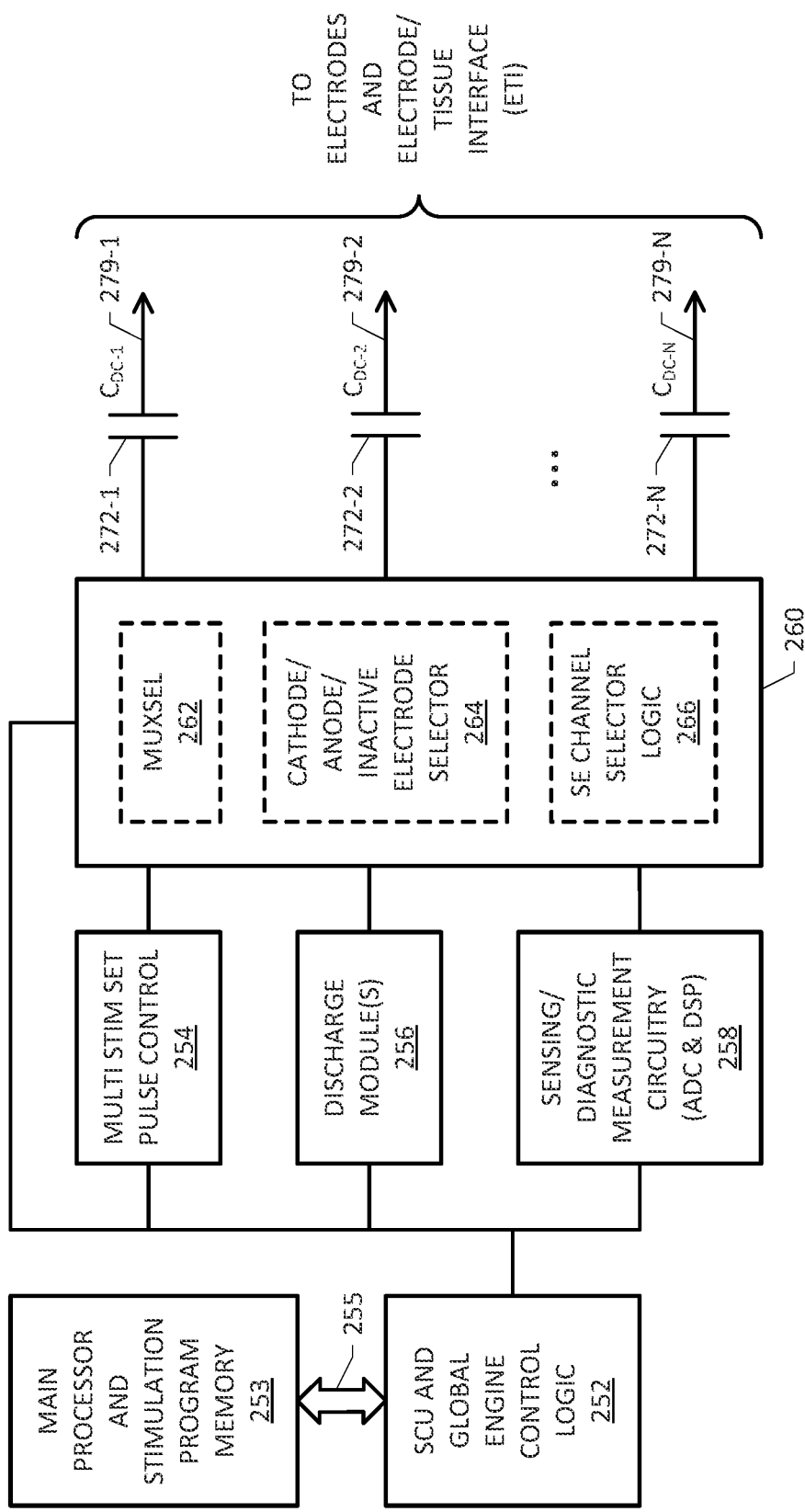
FIG. 2 depicts a block diagram of a pulse generator portion having multiple stimulation engine selection control and associated lead electrode arrangement that may be energized using a custom ISA according to an embodiment of the present patent disclosure.

FIG. 2 depicts a block diagram of a pulse generator portion having multiple stimulation engine selection control and associated lead electrode arrangement that may be energized using a custom ISA according to an embodiment of the present patent disclosure. One skilled in the art will recognize upon reference hereto that various functionalities associated with example blocks shown as part of example pulse generator portion 200 may be distributed and/or integrated among one or more blocks, subsystems and/or modules described hereinabove with respect to FIGS. 1A/1B. Consistent with the description provided in the foregoing sections, a processing unit 252 having or associated with suitable digital control logic is operative as an SCU and global engine control block that is operatively coupled to multi SE pulse control module 254, one or more discharge modules 256 and sensing/diagnostic circuitry 258 for facilitating various functionalities including but not limited to voltage measurements, active discharge cycling, electrode selection and configuration, SE selection, etc. under appropriate programmatic/diagnostics control. An input/output (I/O) interface block 260 is operatively coupled to a plurality of lead connectors 279-1 to 279-N interfaced with respective electrodes, which interfaces may be modeled as suitable lumped-element ETI circuit representations, wherein the lead connectors and associated electrodes may be configured as one or more leads, each having a respective plurality of electrodes. Regardless of the number of leads, a lead connector 279-1 to 279-N may be provided with a DC blocking stimulation capacitor ($C_{DC}$) for facilitating direct current flow blocking functionality with respect to the corresponding electrode that may be configured to operate as a stimulation node. Although some of the electrodes may also be configured to operate as sensing nodes in addition to providing stimulation (e.g., having an AC-coupling sense capacitor ($C_{SENSE}$) in addition to the DC blocking stimulation capacitor), such arrangements are not shown herein without loss of generality. By way of illustration, DC blocking stimulation capacitor $C_{DC-1}$ 272-1 is coupled to lead connector 279-1. Likewise, remaining lead connectors 279-N may be provided with respective $C_{DC-N}$ 272-N to facilitate DC blocking with respect to each corresponding lead electrode thereof.

Interface block 260 may include appropriate multiplexing and selection circuitry 262 and anode/cathode/inactive electrode selection circuitry 264, wherein different electrodes of an electrode grouping of the lead system may be selectively configured for stimulation (e.g., anodic or cathodic stimulation), sensing, or designating unused/inactive states, etc., with appropriate electrical connections being made within an IPG device accordingly relative to the various components therein. In some embodiments, portions of diagnostic circuitry 258 may comprise suitable analog-to-digital converter (ADC) circuitry configured for digital voltage measurement and associated signal processing using known voltage measurement techniques. As such, voltage measurement circuitry can be external and/or internal, on-board or off-board, and/or may be coupled to other measurement devices. Additional details regarding configuring lead electrodes as cathodes or anodes, either during stimulation or for discharging, may be found in may be found in the '643 patent application publication incorporated by reference hereinabove. Still further, an SE selection block 266 may be provided for selectively coupling a (sub)set or portion of lead connectors to a select one of the plurality of SEs under programmatic control, which selection may be effectuated responsive to a therapy program selection from an external programmer (e.g., a clinician programmer or a patient controller) and mediated via suitable programmatic control of SCU/global engine control block 252 according to example embodiments herein. Further, a main processor and stimulation memory block 253 is operatively coupled to SCU/global engine control block 252 via suitable bus architecture 255, which may include ARM-compliant Advanced Microcontroller Bus Architecture (AMBA) or AMBA High-performance Bus (AHB) in some example embodiments.

Figure 3:
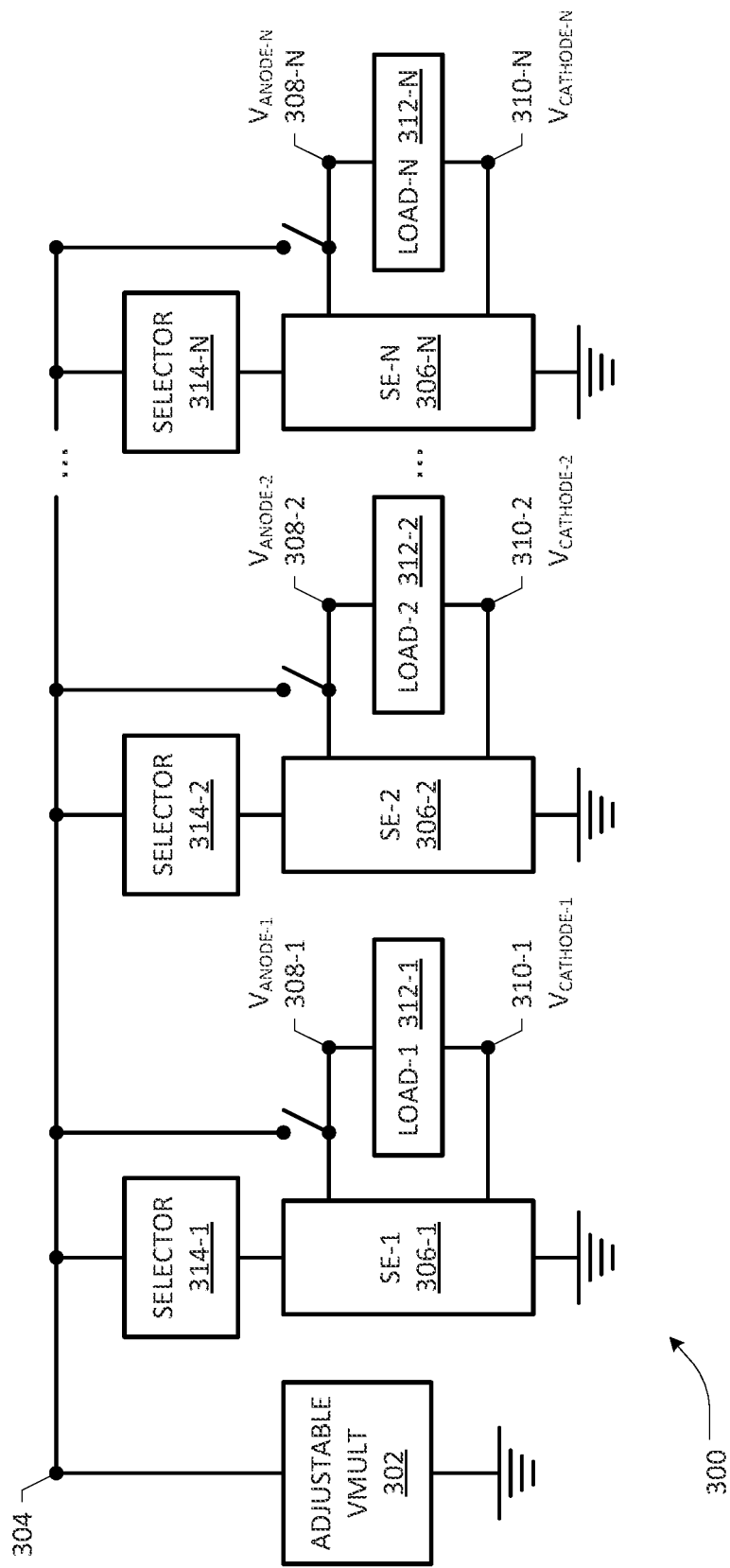
FIG. 3 depicts an example circuit arrangement having multiple stimulation engines that are switchably connectable to a voltage multiplier depending on electrode selection control according to a custom ALLIS executed by a stimulation control unit (SCU) operating as a second processor for purposes of an embodiment of the present patent disclosure.

FIG. 3 depicts an example circuit arrangement having multiple stimulation engines that may be switchably/selectably connectable to a voltage multiplier depending on electrode selection control according to a custom ALLIS executed by an SCU operating as a secondary processor for purposes of an embodiment of the present patent disclosure. An adjustable voltage multiplier (VMULT) 302 may be configured as a charge pump arrangement that can step up or step down from a regulated voltage supply, e.g., from a battery, to provide an output voltage that can cover up to a certain maximum voltage level ($V_{MAX}$) in order to support a sufficient voltage headroom (e.g., 12.0V to 20.0V) for different stimulation settings applicable for a therapy application. For example, a DRG application may require a lower $V_{MAX}$ level than an SCS or DBS application. In one arrangement, VMULT 302 may be implemented as a stacked charge pump capacitor arrangement to provide different output voltages at an output node 304. In general, VMULT 302 may be configured to operate as a voltage supply that may be commonly used by different SEs 306-1 to 306-N to apply stimulation to respective sets of electrodes of a lead system. As illustrated, a plurality of loads 312-1 to 312-N, each representing a respective set of electrodes, are coupled between an anodic node ($V_{ANODE}$) and a cathodic node ($V_{CATHODE}$) of a respective SE. In some embodiments, each SE may be provided with a selector logic module for selectively coupling and/or energizing a select set or portion of the electrodes as the respective load therefor. As shown in FIG. 3, selector logic modules 314-1 to 314-N are operative with respect to corresponding SE modules 306-1 to 306-N. In some embodiments, the overall selection logic functionality may be centrally or commonly provided with respect to all SE modules 306-1 to 306-N as part of an IMD's I/O interface block operative or integrated with a global engine control module. Furthermore, in addition to effectuating the SE selection and/or electrode set selection, suitable digital control logic may be implemented as part of the global engine control in some embodiments in order to generate appropriate control signals for controlling/managing switchable connectivity with respect to each SE in order to couple the anodic node of a selected SE to the output node 304 of VMULT 302 for energizing a corresponding set of electrodes as will be set forth in detail below with reference to an example embodiment.

Figure 4:
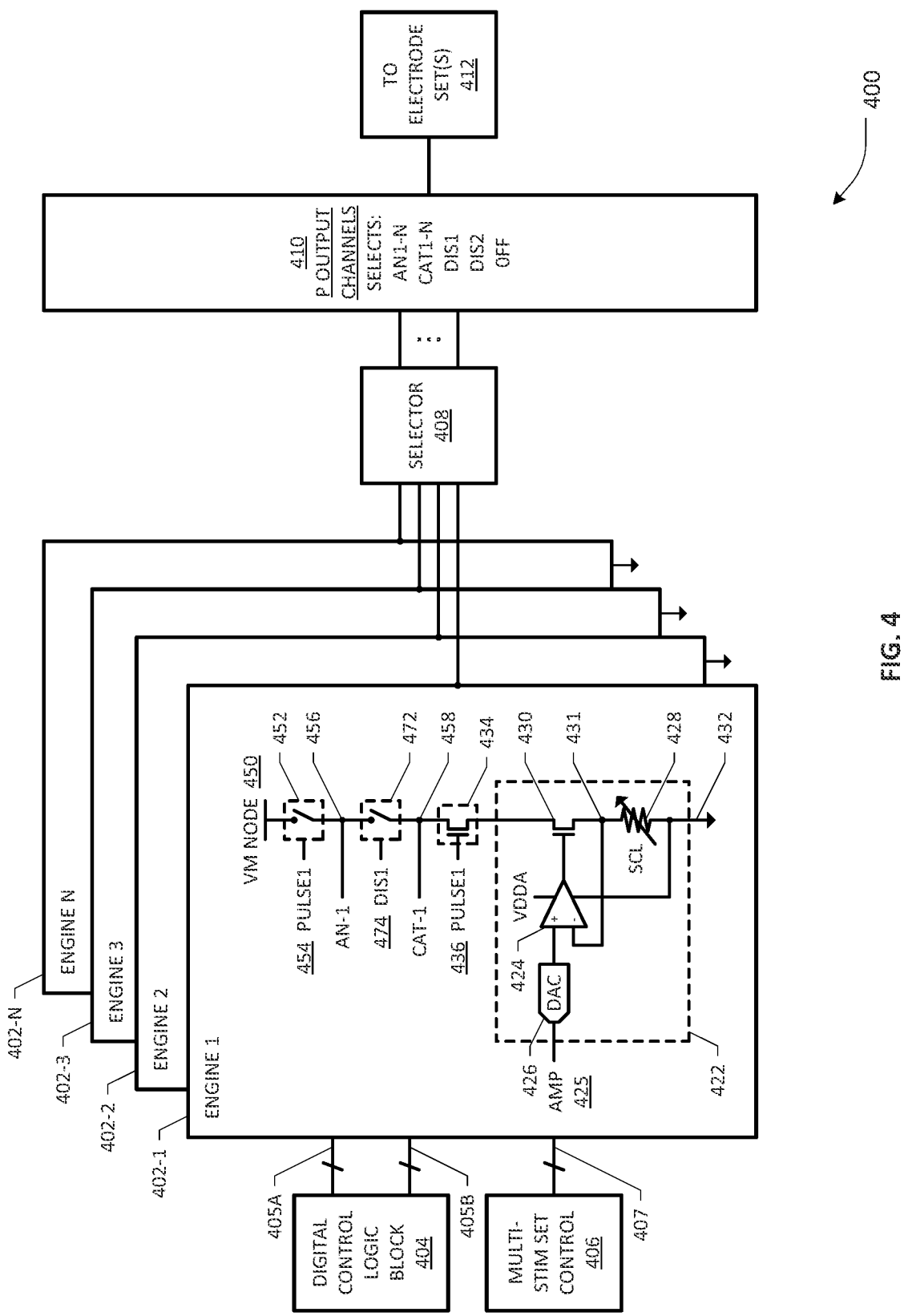
FIG. 4 depicts an example circuit arrangement with additional details of a stimulation engine (SE) that may be operated under control of an SCU for purposes of an embodiment of the present patent disclosure.

FIG. 4 depicts an example circuit arrangement with additional details of a stimulation engine (SE) that may be implemented in multiple SE instances operating under control of an SCU for purposes of an embodiment of the present patent disclosure. A plurality of stimulation engines 402-1 to 402-N are controlled by a digital control logic block 404 and a multi-stim set control block 406 that may be provided in conjunction with or as part of an IMD architecture including SCU/global engine control as discussed above, wherein engines 402-1 to 402-N are substantially analogous to SE modules 306-1 to 306-N of FIG. 3. In one embodiment, each stimulation engine may include a programmable current regulator operative as a current sink circuit, discharge switching circuitry, first switching circuitry configured to switchably connect an anodic node of the stimulation engine to a VM output node operative to supply anodic voltage, and second switching circuitry configured to actuate a switchable coupling between the current sink circuit and a cathodic node of the stimulation engine. In one arrangement, the digital control logic block 404, which may be implemented as a state machine in some embodiments, and a selector module 408 are operative under appropriate timing control for controlling respective stimulation engines 402-1 to 402-N, e.g., independently or otherwise, such that each engine may be activated to stimulate a corresponding set of electrodes independently from or in concert with the remaining stimulation engines based on applicable stimulation settings provided to the respective engines 402-1 to 402-N under multi-stim set control 406. As previously noted, multiple electrode sets 412 of an IMD's lead system may be mapped to different output channels 410, which may be driven by respective stimulation engines under selector control of block 408.

By way of example, stimulation engine 402-1 is shown as including anodic node 456, cathodic node 458, programmable current sink 422, first switching circuitry 452 operative to switchably couple the anodic node 456 to a VMULT/VM connection node 450 that is driven by a common VM output (not shown in this FIG.), second switching circuitry 434 to actuate switchable coupling between the current sink 422 and cathodic node 458, and passive discharge switching circuitry 472 coupled or otherwise disposed between anodic and cathodic nodes 456, 458. It should be appreciated that various switching circuitry blocks of example engine 402-1 may be implemented using a variety of electronic devices such as transistors, diodes, gates, etc. that may be actuated responsive to appropriately timed digital control signals having suitable logic levels depending on whether the stimulation engine is activated for energizing a select set of electrodes mapped to particular channel(s) (i.e., stimulation mode) or rendered in discharge mode (e.g., in an emulated passive discharge (EPD) condition where stimulation of a corresponding electrode set is removed).

In one embodiment, as part of a global engine control functionality, the digital control logic block 404 may comprise circuitry configured to generate a plurality of pulse control signals 405A and discharge control signals 405B for respectively actuating at least a subset of stimulation engines 402-1 to 402-N by providing suitable signals to turn on or off the first and second switching circuitry 452, 434, and passive discharge switching circuitry 472 of the respective stimulation engine depending on whether the stimulation engine is operating in stimulation mode or discharge mode. Further, timing control of the first and second switching circuitry 452, 434 and passive discharge switching circuitry 472 of each respective stimulation engine may be coordinated with the timing of pulse voltage control signals 425 (designated as AMP signals) provided to respective current sink circuitry 422 for achieving synchronized operations of the respective stimulation engine. In one arrangement, digital control logic block 404 and multi-stim set control block 406 may therefore be configured to provide appropriate switch circuitry control signals 405A/405B and pulse setting signals 407 that are coordinated for respective stimulation engines although such switch circuitry control signals 405A/405B and pulse setting signals 407 may be different for different stimulation engines in terms of logic levels, timing control, amplitude/range levels, and the like, so that each stimulation engine's operations for stimulation and/or discharge of associated electrode sets may be independently controlled. Accordingly, in an example scenario, a portion of stimulation engines may be activated for stimulating corresponding sets of electrodes, another portion of stimulation engines may be disposed in a discharge mode for discharging the electrode sets that may have been previously energized by such stimulation engines, while a yet another portion of stimulation engines may not be connected to any electrodes at all (i.e., in inactive or off state), each SE portion operating responsive to suitable engine control signals generated pursuant to the SCU execution of ALLIS-based stimulation instructions and corresponding stimulation/discharge data.

In one example arrangement, each respective stimulation engine, e.g., engine 402-1, is operative to receive from the digital control logic block 404 a first control signal 454 for controlling first switching circuitry 452, a second control signal 436 for controlling second switching circuitry 434, and a third control signal 474 for controlling the passive discharge switching circuitry 472. Depending on the timing and SE selection control, the first and second control signals 454, 436 may be asserted for a select stimulation engine (e.g., engine 402-1), in a stimulation mode, to enable the first and second switching circuitry 452, 434 of the select stimulation engine 402-1 for respectively connecting the VM output connection node 450 to the anodic node 456 and the current sink circuit 422 to the cathodic node 458 in order to facilitate stimulation of a corresponding select set of the electrodes while the third control signal 474 is de-asserted to disable the passive discharge switching circuitry 472 of the select stimulation engine 422. In similar fashion, the first and second control signals 454, 436 may be de-asserted for a select stimulation engine (e.g., engine 402-1), in a passive discharge mode, to disable the first and second switching circuitry 452, 434 of the select stimulation engine 402-1 for respectively disconnecting the VM output connection node 450 from the anodic node 456 and the current sink circuit 422 from the cathodic node 458 while the third control signal 474 is asserted to enable the passive discharge switching circuitry 472 of the select stimulation engine 402-1 for facilitating discharge (e.g., passive discharge) of a corresponding select set of the electrodes.

Skilled artisans will appreciate that logic levels associated with assertion/de-assertion of the various control signals provided in the embodiment of FIG. 4 may be dependent on the type of Boolean logic used relative to the digital electronic devices, transistors, gates, etc., comprising the corresponding switching circuitry respectively actuated thereby. Further, because of the timing synchronization and/or complementary nature of the digital logic involved, control signals 454, 436 (which may be cumulatively referred to as PULSE[1:N] or PLS[1:N] signals with respect to N stimulation engines 402-1 to 402-N) and/or passive discharge control signal 474 (which may be cumulatively referred to as DIS[1:N] signal with respect to N stimulation engines 402-1 to 402-N) may be derived or generated from one another or from one or more signals provided to or from the digital control logic block 404 pursuant to the execution of ALLIS-based stimulation/discharge instructions by the IMD's SCU using the corresponding stimulation/discharge data. Because VM output node connectivity in each stimulation engine may be switched independently depending on the selected electrode set configuration, in addition to the discharge switching functionality also being provided on a per-engine basis, an example implementation of the embodiment shown in FIG. 4 advantageously allows the stimulation engines to share electrodes or be kept completely independent based on the desired therapy. Additionally, multiple stimulation engines may be configured to provide independent therapy to as many target areas in the patient and/or to provide complex stimulation waveforms by means of delivering multi-frequency pulsing signals to the same area that may be designed to interact/interfere with one another in desirable patterns (i.e., stacking of multiple SEs with respect to a single target area in order to achieve what may be termed as "waveform stacking", "waveform nesting" or "waveform engineering", and the like).

In one example implementation, current sink circuit 422 of example engine 402-1 may include a digital-to-analog converter (DAC) 426 interfacing with appropriate pulse voltage control signal 425 (e.g., having suitable magnitude and polarity depending on the type of stimulation current being programmed) to generate a digitally-programmed analog voltage level as an output signal that may be provided to an error amplifier 424. In one arrangement, error amplifier 424 may be implemented as an op amp having two inputs for providing a differential input and operative with a power supply rail voltage VDDA and ground 432 that may be commonly tied to an IMD battery ground along with other ground nodes of remaining stimulation engines. Accordingly, the digitally-programmed analog voltage signal (VDAC) output may be coupled to a first input of error amplifier 424, wherein a second input is coupled to a programmable resistor network 428 operative to provide a digitally-programmed resistance (RSCALE) in a feedback loop arrangement for modulating a current sink output. In general operation, the error amplifier 424 may be programmatically configured to generate a desired amount of stimulation current ($I_{STIM}$), which may be set by the application of Ohm's Law in view of the digitally-programmed resistance RSCALE, where $I_{STIM}$=(VDAC/RSCALE), at a node 431 to which the programmable resistor network 428 is connected. A current conducting device 430 actuated by the output of error amplifier 424 may be coupled to the node 431 for facilitating the stimulation current $I_{STIM}$ flowing through one or more electrodes (i.e., a particular electrode set) when the select stimulation engine, e.g., engine 402-1, is in stimulation mode wherein cathodic node 458 of the select stimulation engine is connected to one side of the selected electrode set and anodic node 456 of the select stimulation engine coupled to the associated electrodes across the ETI interface is connected to the VM output connection node 450 under suitable control signal logic as described above. It should be appreciated that active discharge in an example embodiment may be attained by a stimulation engine by delivering a constant current pulse to the electrodes in a reverse current flow direction—namely, it is achieved by respectively swapping the connectivity of the electrodes programmed as anodes and cathodes via selector block 408 while delivering a constant current pulse with an appropriate VM setting and parameter settings for electrode discharge (e.g., amplitude and pulse width), which may be the same or different than the settings used during stimulation.

Figure 5A:
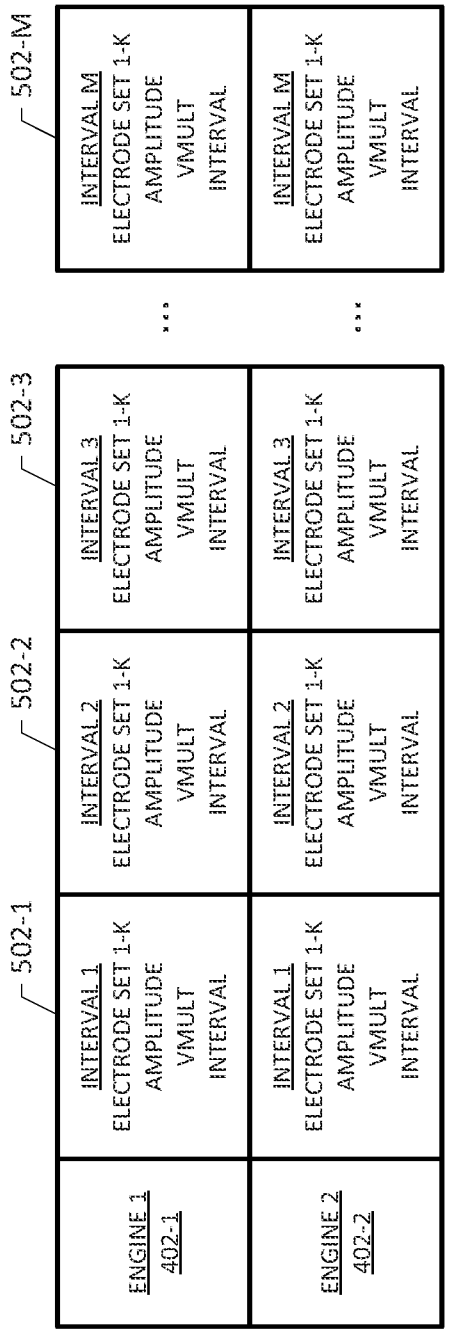
FIGS. 5A and 5B depict example stimulation settings and combination of electrode sets with respect to different stimulation engines in an illustrative scenario according to an implementation of the present patent disclosure.
Figure 5A:
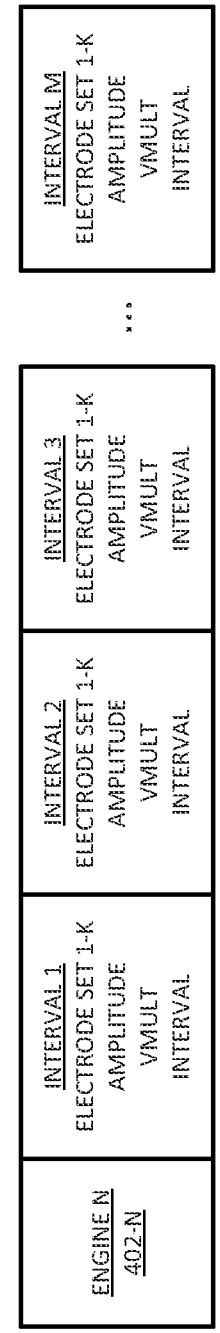
Figure 5B:

FIGS. 5A and 5B depict example stimulation settings and combination of electrode sets with respect to different stimulation engines operating under SCU control in an illustrative scenario according to an implementation of the present patent disclosure. Table 500A of FIG. 5A illustrates engines 402-1 to 402-N, each configurable to provide different stimulation settings 502-1 to 502-M over a plurality of time intervals, wherein each setting may correspond to a particular electrode set (e.g., sets 1 to K, each comprising a particular combination selected from the total number of electrodes of a lead system), pulse amplitude, VM voltage level as well as a corresponding time duration, among others. It should be noted that different stimulation engines may have different settings in respect of any of the parameters thereof based on a combination of pulse definitions and timing definitions obtained from the corresponding therapy program selection. Table 500B of FIG. 5B is illustrative of different electrode patterns and associated electrical parametric ranges, collectively referred to by reference numerals 504-1 to 504-K, corresponding to respective electrode sets (K).

Additional details and/or embodiments of example stimulation engines that may be configured to operate in conjunction with global engine control provided by a secondary processor's ALLIS-based program execution may be found in one or more of the following: (i) U.S. Patent Application Publication No.: US20210252291A1, entitled, "NEUROMODULATION THERAPY WITH A MULTIPLE STIMULATION ENGINE SYSTEM"; and (ii) U.S. Patent Application Publication No.: US20210236822A1 entitled, "IMPLANTABLE PULSE GENERATOR WITH MULTIPLE STIMULATION ENGINES"; each of which is incorporated herein by reference.

Figure 6:
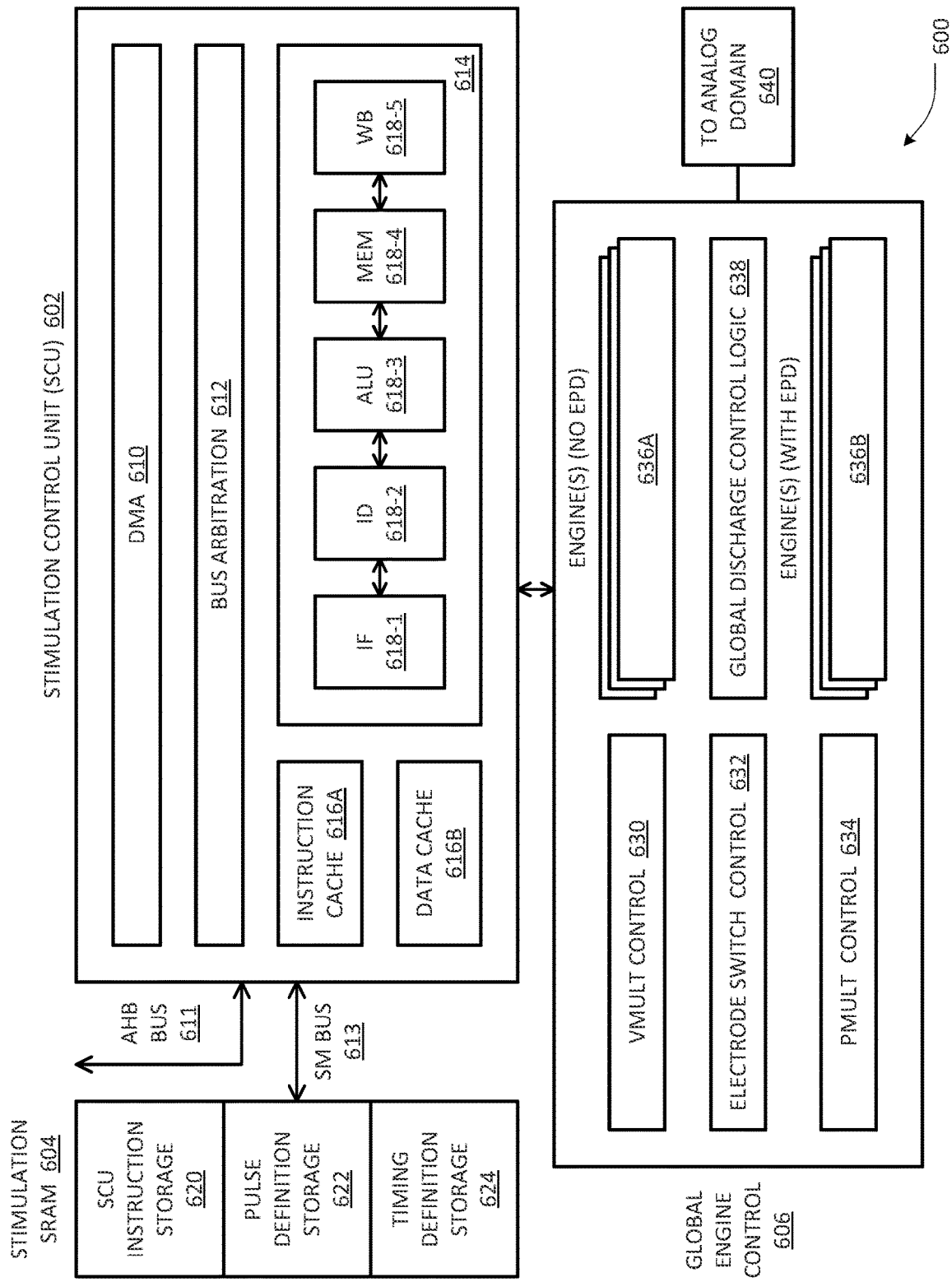
FIG. 6 depicts a block diagram of an IMD portion illustrating one or more storage areas, an example SCU and a global engine control block according to an embodiment of the present patent disclosure.

FIG. 6 depicts a block diagram illustrative of an IMD portion that exemplifies one or more storage areas, an example SCU and a global engine control block, wherein the SCU is configured to execute stimulation code using instruction pipeline architecture for energizing one or more SEs according to an embodiment of the present patent disclosure. A storage area 604 of IMD portion 600 is exemplary of a persistent memory space (e.g., SRAM) organized in any suitable architecture (e.g., a paged or index addressing architecture) that may be configured to store SCU instructions (e.g., provided as assembled ALLIS program code) in an instruction storage space 620, a plurality of pulse definitions in a pulse definition storage space 622, and a plurality of timing definitions in a timing definition storage space 624, as well as any additional storage. Pulse and timing definition storage spaces 622, 624 may also be referred to as stimulation data storage for purposes of some embodiments of the present patent disclosure. SCU 602 may comprise any suitable microprocessor/microcontroller operative with a clock/oscillator system having a lower frequency than that of a main MCU's clock as previously mentioned. In one arrangement, SCU 602 is operatively coupled to the IMD's main MCU (not shown in this FIG.) via a high-performance inter-processor bus 611 (e.g., an AMBA bus as previously described) as well as a memory access bus 613 for communicating with storage area 604. Depending on implementation, buses 611, 613 may be operative at different clock speeds, wherein bus access control may be facilitated by a bus arbitration unit 612. A direct memory access (DMA) subsystem 610 may be provided to facilitate intra- and/or inter-chip data transfers, including, e.g., memory-to-memory transfers, using external buses or internal buses that may be configured to effectuate appropriate DMA channels. In one example implementation, instruction cache 616A and data cache 616B may be provided as hardware or software components of SCU 602 configured to store stimulation instructions and/or stimulation data retrieved from stimulation storage space 604 in order to facilitate quicker processing of the instructions by an execution unit 614, which may be based on a pipeline architecture. Accordingly, future requests for an instruction and/or data can be served within the timing constraints while still based on the slower clock frequency of SCU 602 in such an arrangement. In some implementations, the data stored in data cache 616B may be the result of an earlier computation or a copy of data stored elsewhere, e.g., in an external memory. A cache hit occurs when the requested item (e.g., an ALLIS instruction in machine code or a data value) can be found in respective caches 616A, 616B. Otherwise, a cache miss is encountered and the requested item may need to be fetched from a storage space, e.g., stimulation SRAM 604. Depending on a particular SCU architecture and therapy program implementation, access patterns relating to the requested instructions and/or data may exhibit temporal locality (e.g., where the item is requested that has recently been requested already) and/or spatial locality (e.g., where the item is requested that is stored physically close to an item that has already been requested).

In one arrangement involving pipeline execution, the instruction execution unit 614 may be comprised of an architecture for facilitating instruction-level parallelism that divides incoming instructions into a series of sequential steps (e.g., a "pipeline") performed by different portions of the processor execution unit with different parts of instructions processed in parallel. By way of illustration, the following components are exemplified in FIG. 6: an Instruction Fetch (IF) component 618-1 operative to read an instruction from an address (e.g., in a cache address) in a first clock cycle; an Instruction Decode (ID) component 618-2 operative to decode the instruction in a second clock cycle, wherein a register file may be accessed to obtain the values from the registers used in the instruction; an Arithmetic Logic Unit (ALU) component 618-3 operative to perform in a third clock cycle one or more basic arithmetic functions (i.e., addition, subtraction, multiplication, and division), register shift/rotate operations, and/or certain logic operations (e.g., AND, OR, etc.) on the data/operand of the instruction; a Memory Access (MEM) component 618-4 operative in a fourth clock cycle for reading/writing from/to the memory based on the operands present in the instruction; and a Write Back (WB) component 618-5 operative in a fifth clock cycle for writing the computed/fetched value to a register identified in the instruction.

A global engine control block 606 coupled to SCU 602 is operative as an interface between the digital domain of SCU operations and an analog functional domain 640 involving the stimulation portion of the IMD's output driver circuitry. In one arrangement, a plurality of logic and interface modules may be provided as part of global engine control block 606 that may be configured to operate responsive to the output of SCU processing, whereby various control signals may be generated for facilitating SE selection, loading of appropriate pulse/timing parameters to the SEs, electrode/output node selection control, and the like, as previously set forth. By way of illustration, a VMULT control block 630, an electrode switch control block 632, a PMULT control block 634, as well as a global discharge control logic block 638 are provided for controlling the stimulation and/or discharge functionalities of a plurality of stimulation engines. In one arrangement, the overall control logic of global engine control 606 may be configured to support a first (sub)set of SEs 636A having no discharge capability (e.g., without EPD), a second (sub)set of SEs 636B having EPD capability, and any combination thereof, wherein PMULT control may be configured to facilitate selecting the input voltage of a multiplier (e.g., VM 175 shown in FIG. 1B) from different settings (e.g., ½VBAT, VBAT, 2VBAT, etc.) to reach lower or higher resolution VMULT steps for utilizing as output voltage(s) that may be adapted to drive respective anodes of the individual SEs.

Figure 7:
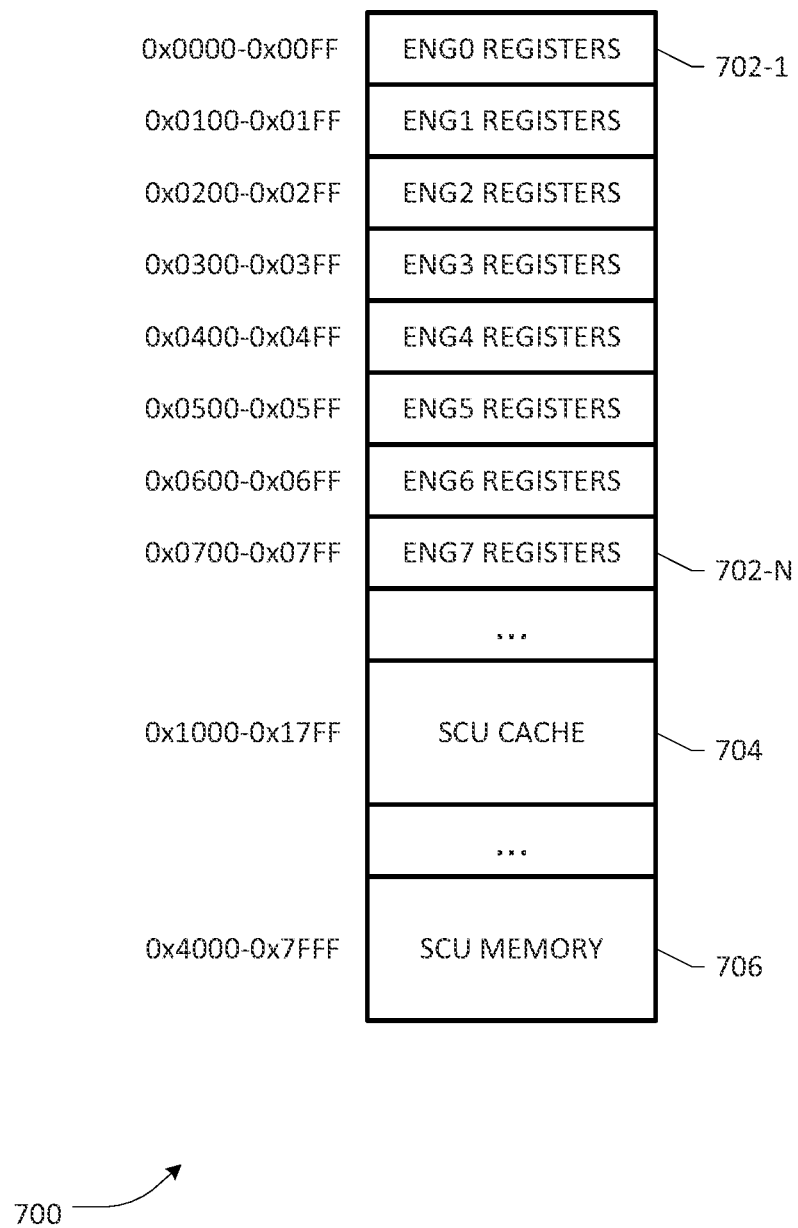
FIG. 7 illustrates an example storage space that may be configured into various storage areas or portions operative with an SCU for purposes of an embodiment of the present patent disclosure.

FIG. 7 illustrates an example storage space 700 that may be logically configured into various storage areas or portions having a suitable addressing scheme or mapping operative with an SCU for purposes of an embodiment of the present patent disclosure. Storage space 700 may be partitioned to support a plurality of register groups 702-1 to 702-N depending on how many SEs are implemented in an IMD, wherein each register group may comprise a (sub)plurality of registers (e.g., 32-bit, 64-bit, etc.) that may hold or be loaded with appropriate stimulation data with respect to a corresponding SE, respectively. A cache space 704 associated with the SCU is exemplary of instruction cache 616A and data cache 616B shown in FIG. 6 in one example arrangement. In similar fashion, a memory space 706 accessible by the SCU is illustrative of persistent memory 604 shown in FIG. 6.

In one arrangement, the register space associated with an SCU of the present patent disclosure may be configured as one or more global registers for holding data used by all SEs of the IMD, in addition to being partitioned into local registers containing values that are used by a specific SE. As such, registers may contain data that the processor is currently processing whereas a cache/memory may contain data that may be required for processing at a later time. Depending on implementation, registers may include data registers, address registers, instruction registers, input/output registers, accumulators, etc. Further, an SCU may include a register control logic module for effectuating rules as to which entity can access global registers, local registers, or any combination thereof, and at what times during the execution of a stimulation program.

Figure 8:
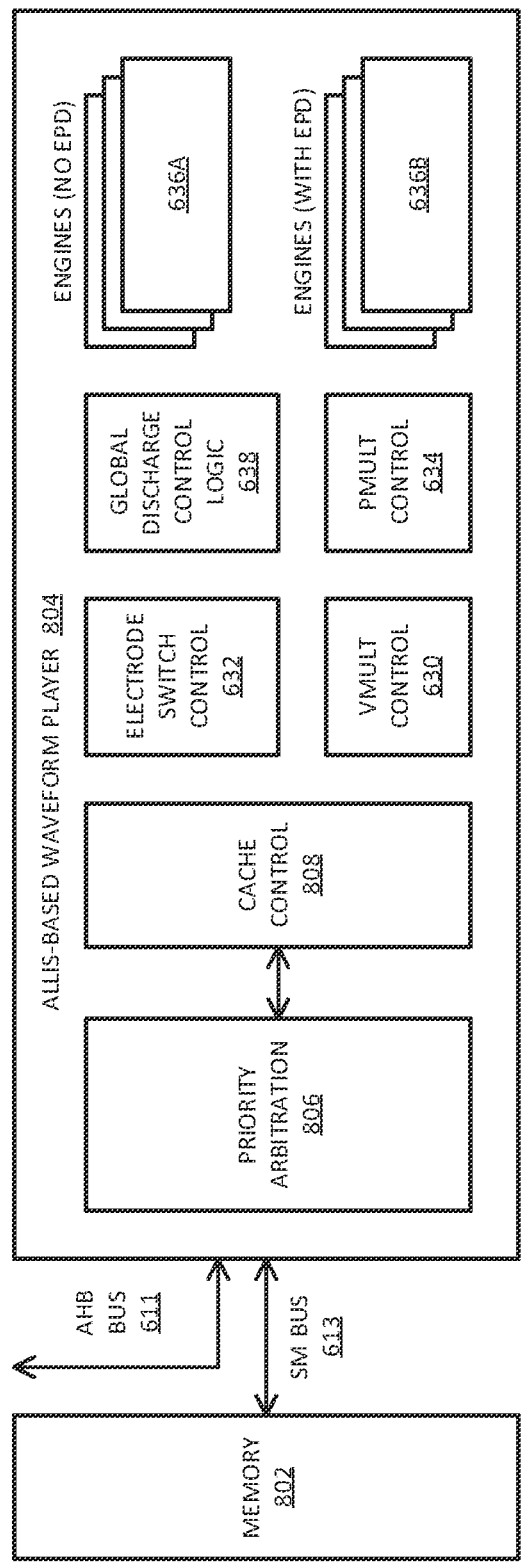
FIG. 8 depicts a block diagram illustrating SCU operation as an ALLIS-based waveform player configured to energize one or more SEs according to an embodiment of the present patent disclosure.

FIG. 8 depicts a block diagram illustrating SCU operation as an ALLIS-based waveform player configured to energize one or more SEs according to an embodiment of the present patent disclosure. Arrangement 800 includes a persistent memory 802 that may be organized to contain various storage portions as set forth above, wherein a waveform player 804 may be configured to communicate with persistent memory 802 as well as a main processor, e.g., via bus 613 and bus 611 as previously noted. In one arrangement, an assembled/compiled ALLIS program may be stored or transported into at least a portion of memory 802 as a "program record", which may be executed for generating a pre-specified stimulation pattern having specific definitions of pulse characteristics and timing intervals. In some example embodiments, a program record may be played until completion or may continue to be played in a loop depending on the information provided in the program record. This concept may be referred to as a "waveform player playback", wherein an implementation of waveform player 804 may be configured to provide the flexibility and versatility of stimulation intended to support existing as well as future stimulation needs in a therapy application scenario while providing a low power solution to stimulation (e.g., because of program execution by a lower frequency and low current secondary processor).

In one implementation, waveform player 804 may include bus priority arbitration 806 as well as a cache control block 808 for accessing the instructions and data either from persistent memory 802 and/or an external memory (not shown in this FIG.), which may in turn depend on cache hits or misses. Waveform player 804 may further include various logic control blocks, e.g., VMULT control block 630, electrode switch control block 632, PMULT control block 634, as well as global discharge control logic block 638 as part of global engine control functionality with respect to SEs 636A/636B as previously described.

Skilled artisans will recognize upon reference hereto that an ALLIS implementation according to the teachings herein advantageously provides a "hardware abstraction" layer operative to convert or otherwise interpret the contents of a stimulation memory into commands, settings and/or controls for instructing or configuring an SE in order to generate a pulse in accordance with a particular PD/TD information on a pulse-by-pulse and/or engine-by-engine basis in an exemplary multi-engine therapy system, wherein the drawbacks potentially emanating from continuously involving a main processor in the generation of stimulation pulses may be advantageously mitigated.

Figure 9:
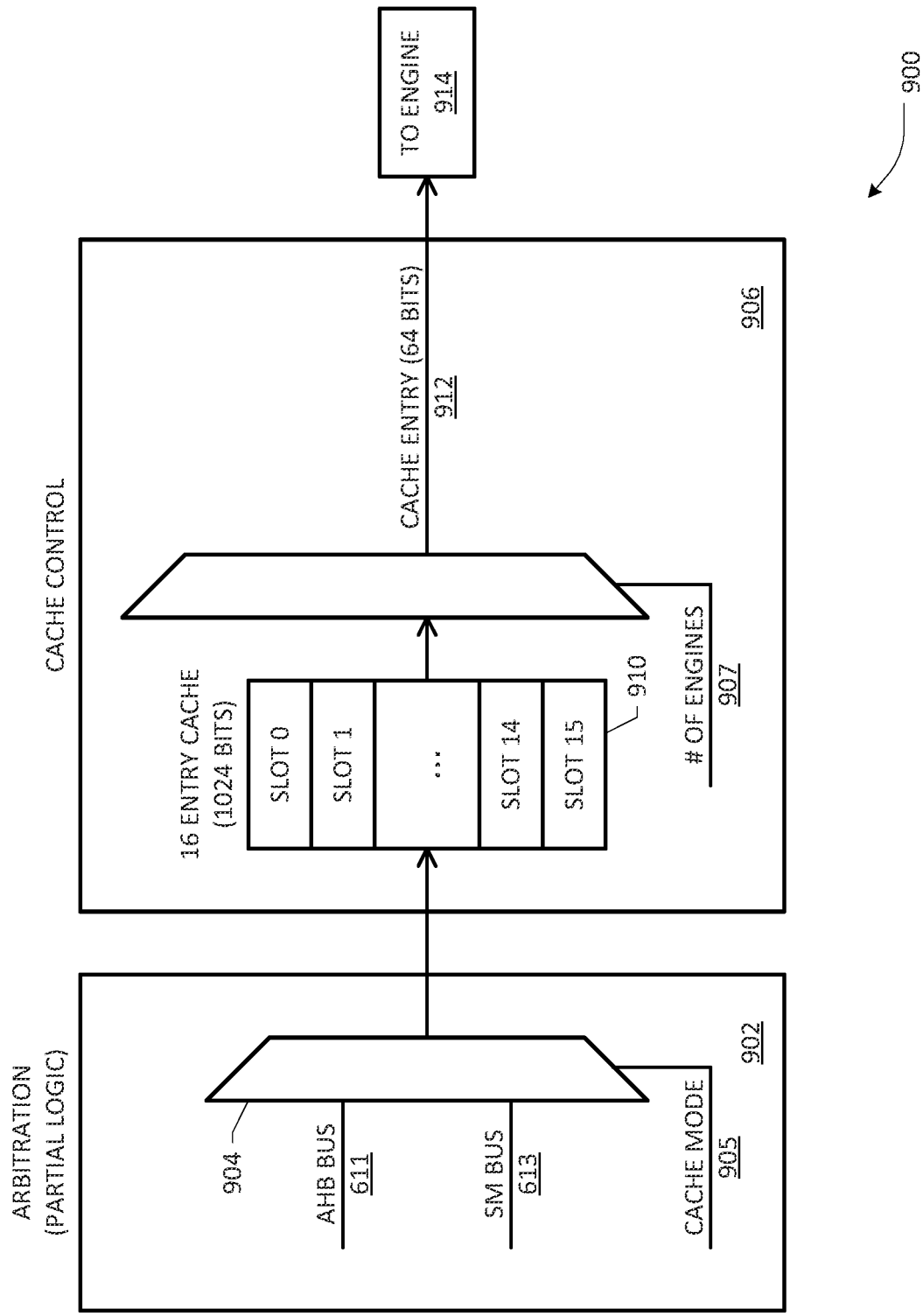
FIG. 9 depicts a block diagram illustrating cache control for facilitating SCU operation according to an embodiment of the present patent disclosure.

FIG. 9 depicts a block diagram illustrating cache control for facilitating SCU operation according to an embodiment of the present patent disclosure. Arrangement 900 includes a cache control module 906 operative in association with a bus arbitration logic module 902 for providing/accessing required/requested item with respect to a select SE block 914. At least a portion of arbitration logic module 902 includes a multiplexer 904 (e.g., a first MUX) operating responsive to a cache mode control signal 905, wherein data received via either bus 611 or bus 623 is selected and forwarded to an N-entry cache 910 (e.g., organized as a 16-slot cache) of cache control module 906. An engine select control signal 907 is operative to control a multiplexer 907 (e.g., a second MUX) for selecting a particular slot and forwarding its contents via output path 912 with respect to the selected SE block 914.

Figure 10:
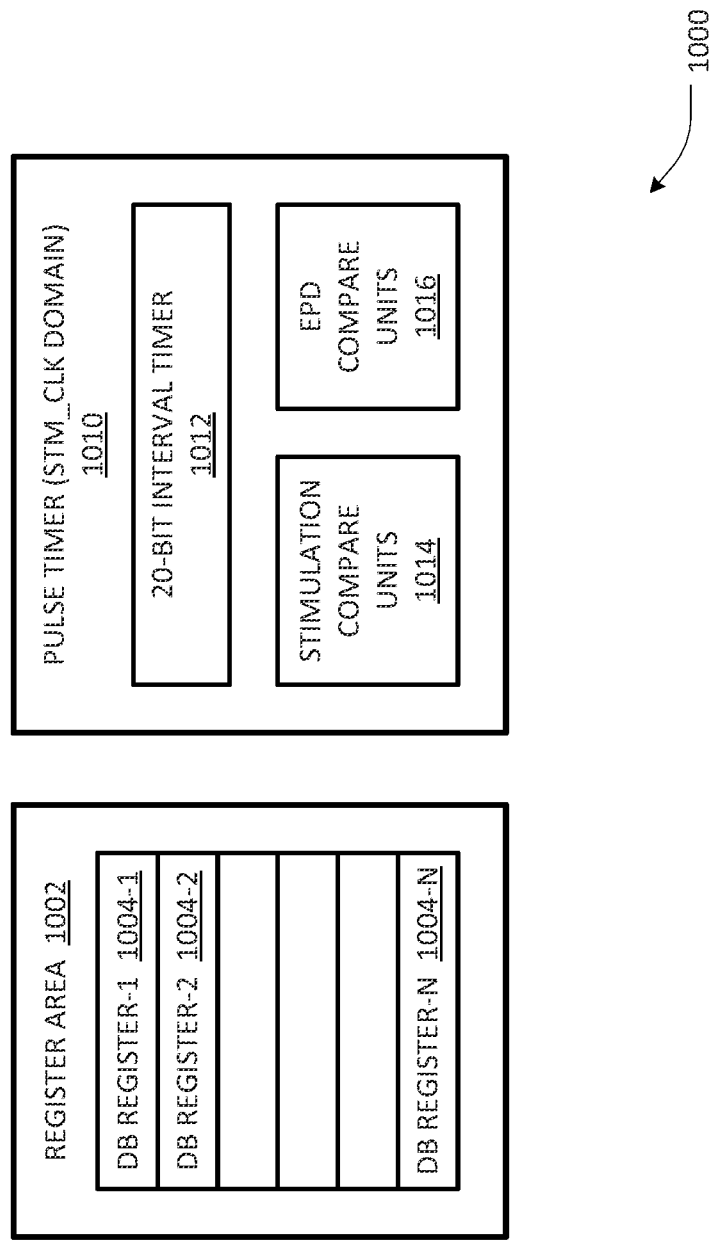
FIG. 10 depicts a block diagram of a engine control module for with respect to a select SE according to an embodiment of the present patent disclosure.

FIG. 10 depicts a block diagram of an engine control module for facilitating SCU operation according to an embodiment of the present patent disclosure. Engine control module 1000 includes a register area 1002 comprising a plurality of registers 1004-1 to 1004-N configured to store data received from the ALLIS-based SCU waveform player with respect to a select SE as described above. In one arrangement, registers 1004-1 to 1004-N may be implemented as double-buffered registers such that data in one buffer may be processed while a next set of data is read into the other one. A pulse timer control module 1010 is operative with a stimulation clock domain that may be derived from the SCU's clock in some arrangements. An N-bit internal timer 1012 is operative to provide a time base for stimulation and discharge operations, which may be facilitated by respective timing compare units 1014, 1016.

Turning to FIGS. 11A and 11B, depicted therein are example ALL instructions and corresponding machine code implementations according to an embodiment of the present patent disclosure. At least a partial set of ALLIS mnemonic code portion 1100A is exemplified in FIG. 11A, wherein a human-friendly version is provided with respect to a plurality of instructions having respective symbolic names. A machine language (or machine code) version of the instructions in a more complete form (e.g., including respective opcode and operand fields) is illustrated as a 32-bit machine code representation 1100B in FIG. 11B. SLP instruction 1102 is operative to cause an SE to wait for a time period specified by an OFFSET parameter. Corresponding machine code representation 1122 includes a 4-bit opcode, with remaining bits allocated for identifying an OFFSET from a global timer (e.g., a timer being commonly used for all SEs in one representative embodiment) that may be derived from or otherwise based on the SCU's clock. LOAD instruction 1104 is operative to cause loading of an SE with a particular TYPE of stimulation data. In one implementation, TYPE can be either a pulse definition (PD) or a timing definition (TD), each being identified numerically or otherwise via a suitable address. If there is a cache miss, a memory access may be required as previously noted. Once a TD or PD is obtained, its value is loaded to a TD register or a PD register of the selected SE, respectively. Responsive thereto, appropriate control logic associated with the SE may be executed to perform the required operation (e.g., generating a pulse having the characteristics according to the loaded PD and TD data). Corresponding machine code representation 1124 shown in FIG. 11B includes a 4-bit opcode, 4-bit engine identifier field, 4-bit TYPE field, followed by a value/address for locating the specified PD or TD. In similar fashion, STORE instruction 1106 is operative to cause storing an engine's PD or TD (depending on a TYPE parameter) at a particular location in a main memory or some other location depending on implementation. Machine code representation 1126 corresponding to STORE instruction 1106 shown in FIG. 11B includes a 4-bit opcode, 4-bit engine identifier field, 4-bit TYPE field, followed by a value/address of a memory location for storage.

ALU instruction 1108 is operative to perform one or more ALU operations (e.g., arithmetic operations, increment/decrement operations, shift/rotate operations and/or digital logic operations, etc.) on one or more registers with respect to a specific SE, whereby a particular SE's operation may be selectively and dynamically modified/adjusted without the intervention of a main processor. For example, in one implementation, the contents of a TD register or a PD register associated with the selected SE may be modified so as to affect the operation of that SE (e.g., pulse generation or EPD operation) while the operation of the rest of the SEs remains unaffected. If no engine is specified, the requested ALU operation may be performed on a global level (i.e., applied to all SEs). Machine code representation 1128 corresponding to ALU instruction 1108 is shown in FIG. 11B, which includes a 4-bit opcode, 4-bit engine identifier field, 4-bit ALU operation type, a 4-bit attribute (ATTR) field identifying whether a TD, PD or some other pulse attribute required to be operated upon, followed by a value. RPT instruction 1110 is operative to cause branching in the program flow until a repeat counter value is reached (e.g., decremented to 0), wherein the repeat counter value may be set via a special ALU instruction. Machine code representation 1130 corresponding to RPT instruction 1110 is shown in FIG. 11B, which includes a 4-bit opcode and an 8-bit field identifying an instruction to which program control is branched, followed by a field of unused bits. Although not specifically exemplified here, a BRANCH or BR instruction may also be configured to cause branching in the program flow that is operative similar to RPT. For instance, a BR NEG instruction may be implemented such that if the last instruction happened to cause a condition code value of the processor to be below 0, then program flow control may branch to a specific instruction identified in the BR instruction.

Skilled artisans will recognize that the foregoing ALLIS code is set forth by way of illustration only and not intended to be limiting. As a customizable ISA, an implementation of ALLIS code may involve instructions having different syntax, e.g., mnemonics and symbolic names, depending on a particular IMD, which may be assembled into machine code (e.g., hex files) specific to the SCU.

In one arrangement, stimulation data comprising various types of pulse and timing definitions as well as electrode and engine definitions, and the like, may be stored in a data storage space (e.g., distributed, integrated or contiguous) that is populated by a main MCU for subsequent access or transport by or to the SCU for facilitating stimulation therapy according to the teachings herein. An example 32-bit pulse definition may be configured to include a plurality of attributes or characteristics defined over respective bitfields, e.g., an amplitude in 11 bits, a pulse width in 8 bits, an ADC offset in 8 bits, an ADC repeat count in 5 bits, etc. An example electrode definition may include a 2-bit mode field (to define Off; Anode; Cathode; and Anode configuration of an electrode) as well as a mode-dependent 8-bit field wherein if a Cathode is configured, 8 bits represent 0-7 connections; if a Discharge is configured, first two bits may be configured to identify discharge rails of an IMD, etc. An example 32-bit timing definition may include a 24-bit pulse interval field, a 3-bit mode identifying timing-related operations with respect to the generated pulses such as one-shot, repeating, burst (intra-burst and/or inter-burst), or abutted, etc., a 4-bit field identifying a repeat count, and a 1-bit field indicating a logic invert operation of the timing signal, wherein each operation mode may be further defined. An example target area definition may include a configurable bitfield depending on how many electrodes are being utilized for stimulating a target area. By way illustration, a 10-bit field may be provided for indicating a total number of electrodes, each of which may be configured separately based on respective electrode definitions set forth above, e.g., 10 bits per electrode. An example engine definition may include a 2-bit field pulse definition attribute to identify a current PD and a next PD, a 2-bit timing definition attribute to identify a current TD and a next TD, a 1-bit area pointer to identify an area definition, a 5-bit AMP_EN Offset field to indicate the time from enabling a stimulation amplifier to the pulse generation, a 12-bit Delayed Discharge field to identify the time from end of pulse to start of discharge, as well as appropriate bitfields to specify the time EPD is on and any offset fields. Example global definitions may include a global timer (in 32 bits), an 8-bit engine field indicating the number of SEs, a 16-bit area field to indicate the number of areas, as well as appropriate bitfields to indicate respective maximum numbers of PDs, TDs and instructions per program, etc.

FIG. 12 depicts an example 32-bit data packet 1200 including timing definition data 1202, pulse definition data 1204, electrode area data 1206 and ADC data 1208 that may be transmitted, retrieved or otherwise obtained by or from an SCU for purposes of an embodiment of the present patent disclosure.

Figure 13:
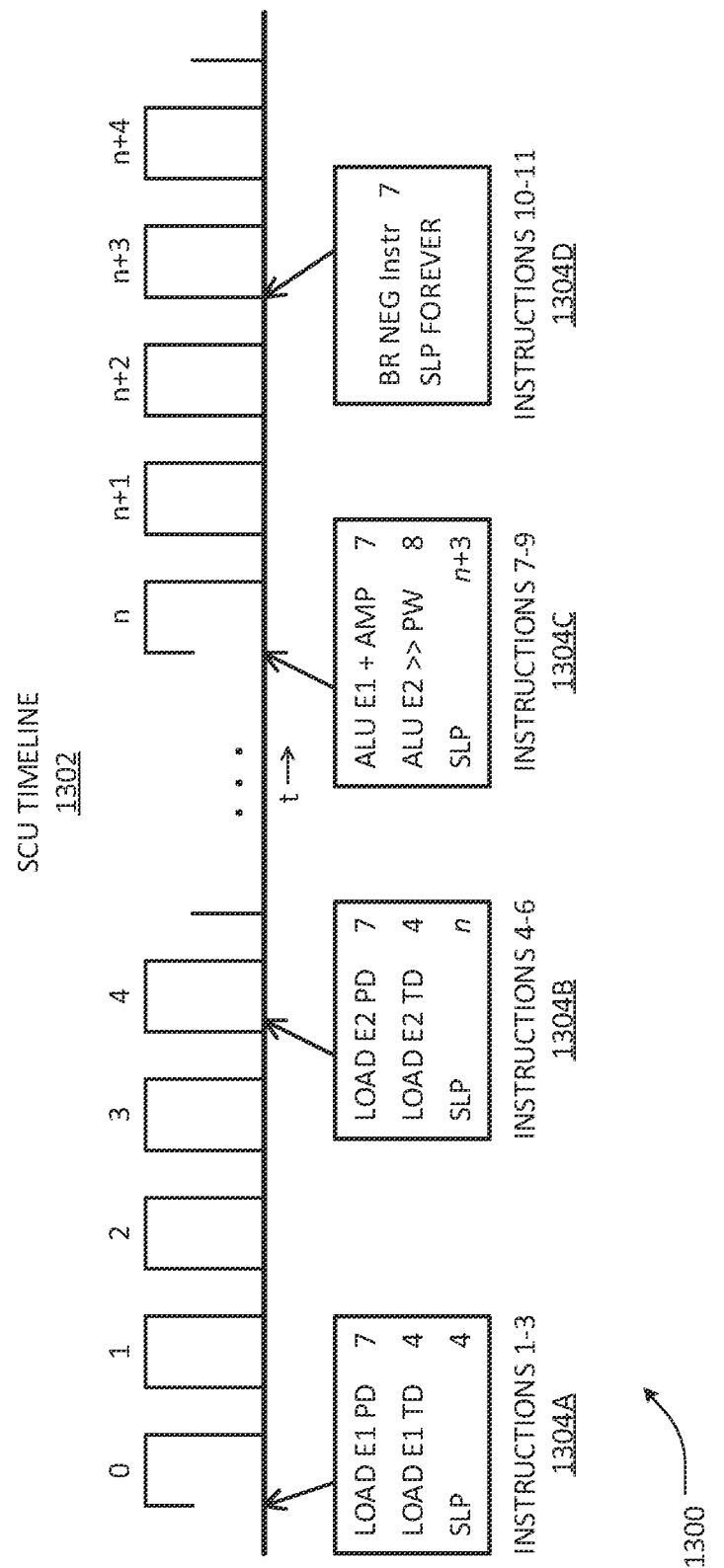
FIG. 13 depicts an execution sequence of a plurality of ALL instructions in an illustrative scenario according to an embodiment of the present patent disclosure.

FIG. 13 depicts an example instruction pipeline 1300 that may be executed using a time base provided by an SCU operating at a slower clock frequency in an illustrative scenario. A plurality of ALL instructions are shown as Instructions 1-11 that may be grouped into four portions 1304A-1304D, which may be executed at different times based on a clock 1302 operating as a global timeline. At a clock edge of first clock cycle 0 (e.g., a rising edge thereof), code portion 1304A comprising the following Instructions 1-3 may be executed:

| Instructions 1-3 | | |
|---|---|---|
| LOAD E1 | PD | 7 |
| LOAD E1 | TD | 4 |
| SLP | | 4 |

Pursuant to executing Instructions 1-3, engine E1 is loaded with a PD identified as 7 and a TD identified as 4, followed by SCU wait period of 4 clock cycles. A pulse waveform based on the attributes defined by the PD and TD contents/values may be generated by E1 for energizing one or more electrodes coupled to E1. At a clock edge of clock cycle 4 (e.g., a rising edge thereof), code portion 1304B comprising the following Instructions 4-6 may be executed:

| Instructions 4-6 | | |
|---|---|---|
| LOAD E2 | PD | 7 |
| LOAD E2 | TD | 4 |
| SLP | | n |

Pursuant to executing Instructions 4-6, engine E2 is also loaded with a PD identified as 7 and a TD identified as 4, followed by SCU wait period of predetermined n clock cycles. Accordingly, a second pulse waveform based on the attributes defined by the PD and TD contents/values may be generated by E2 for energizing one or more electrodes coupled to E2. At a clock edge of clock cycle n (e.g., a rising edge thereof), code portion 1304C comprising the following Instructions 7-9 may be executed for adjusting the characteristics and attributes of the two pulses generated by engines E1 and E2 by way of ALU operations:

| Instructions 7-9 | | |
|---|---|---|
| ALU E1 + AMP 7 | | |
| ALU E2 >> PW8 | | |
| SLP n + 3 | | |

By executing the ALU operations, the amplitude of the pulse generated by engine E1 is increased by a certain level as defined or identified by AMP 7, while the width of the pulse generated by E2 is increased to a value that is greater than a value as defined or identified by PWB. The SCU execution thereafter may wait for three additional clock cycles of timeline 1302, whereupon instruction group 1304D comprising the following instructions may be executed:

| Instructions 10-11 | |
|---|---|
| BR NEG | Instr 7 |
| SLP | FOREVER |

By executing a Branch instruction, SCU program flow control may be passed to executing from a known location in the sequence, e.g., a previous instruction such as, e.g., Instruction 7, thereby causing an increase in the amplitude of the pulse generated by E1 in the embodiment illustrated herein. Thereafter, ALLIS execution by the SCU may cease until further control signals or interrupts are received.

In one arrangement, the SCU may be configured to perform a verification at each edge of clock 1302 (which is based on the slower oscillator) to determine if there are pending instructions to be executed. If there is a pending instruction and any associated operands already exist in the SCU's cache (i.e., a cache hit), such instructions may be executed accordingly. On the other hand, if there a cache miss, the faster oscillator may be enabled to fetch the data from an external memory.

Figure 14:
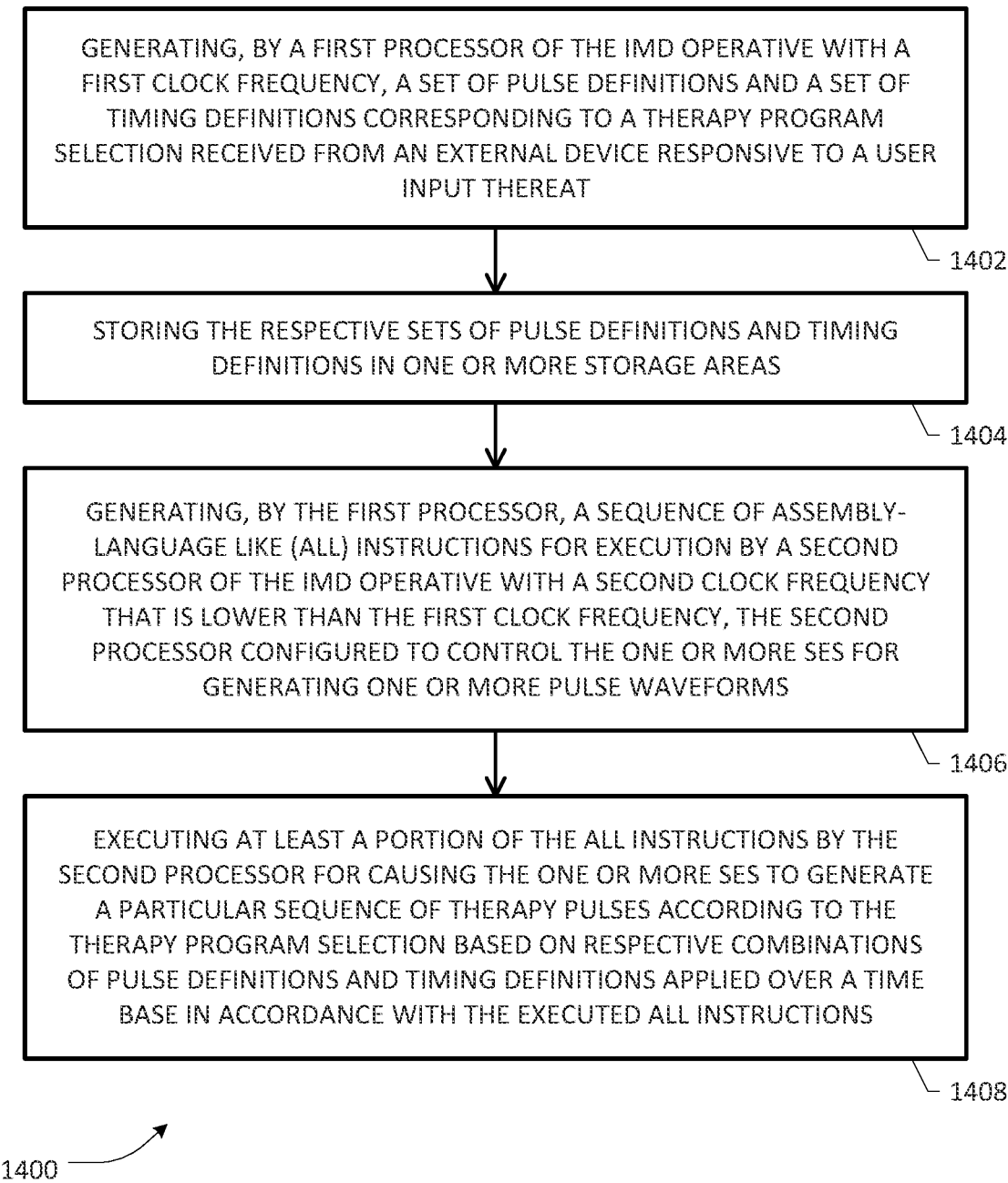
FIG. 14 depicts a flowchart of blocks, steps and/or acts that may be (re)combined in one or more arrangements, e.g., with other flowcharts, for facilitating a stimulation therapy method using a custom ALLIS architecture of an IMD according to some embodiments of the present patent disclosure.

FIG. 14 depicts a flowchart of blocks, steps and/or acts that may be (re)combined in one or more arrangements, e.g., with other flowcharts, for facilitating a stimulation therapy method using a custom ALLIS architecture of an IMD according to some embodiments of the present patent disclosure. Example process 1400 may involve, generating, by a first processor of the IMD operative with a first clock frequency, a set of pulse definitions and a set of timing definitions corresponding to a therapy program selection received from an external device (e.g., a clinician programmer or a patient controller) responsive to a user input thereat, as set forth at block 1402. At block 1404, the respective sets of pulse definitions and timing definitions may be stored in one or more storage areas depending on the IMD's memory architecture. At block 1406, the first processor generates a sequence of ALL instructions for execution by a second processor of the IMD, wherein the second processor is operative with at least a second clock frequency that is lower than the first clock frequency. As described in detail hereinabove, the second processor may be configured to control one or more SEs of the IMD for generating one or more pulse waveforms. At block 1408, at least a portion of the ALL instructions may be executed by the second processor (e.g., responsive to a control signal received from the first processor) for causing the one or more SEs to generate a particular sequence of therapy pulses according to the therapy program selection based on respective combinations of pulse definitions and timing definitions applied over a time base in accordance with the executed ALL instructions.

Figure 15A:
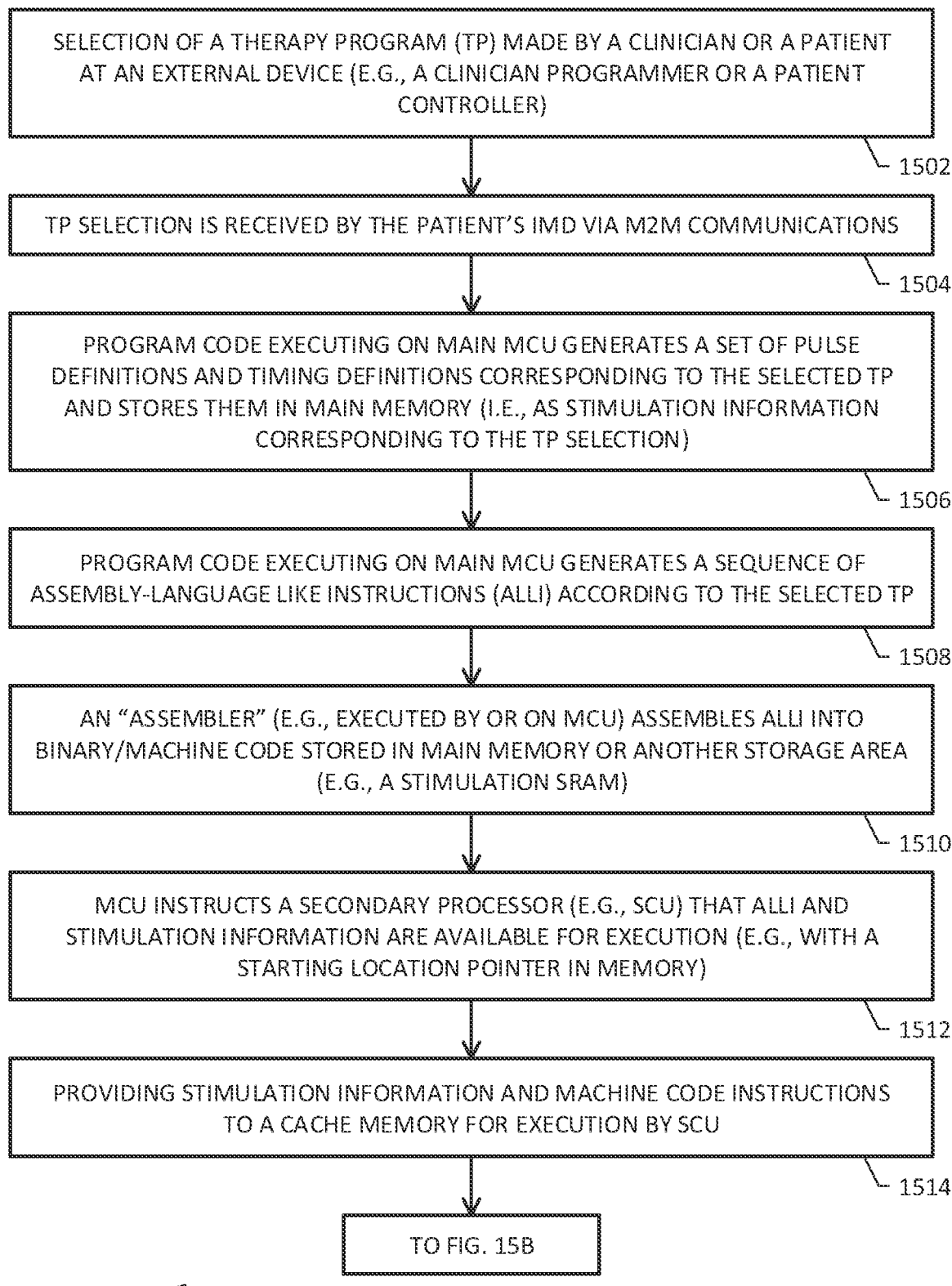
FIGS. 15A and 15B depict a flowchart of blocks, steps and/or acts that may be (re)combined in one or more arrangements, e.g., other flowcharts, for facilitating a stimulation therapy method using a custom ALLIS architecture of an IMD according to some embodiments of the present patent disclosure.
Figure 15B:
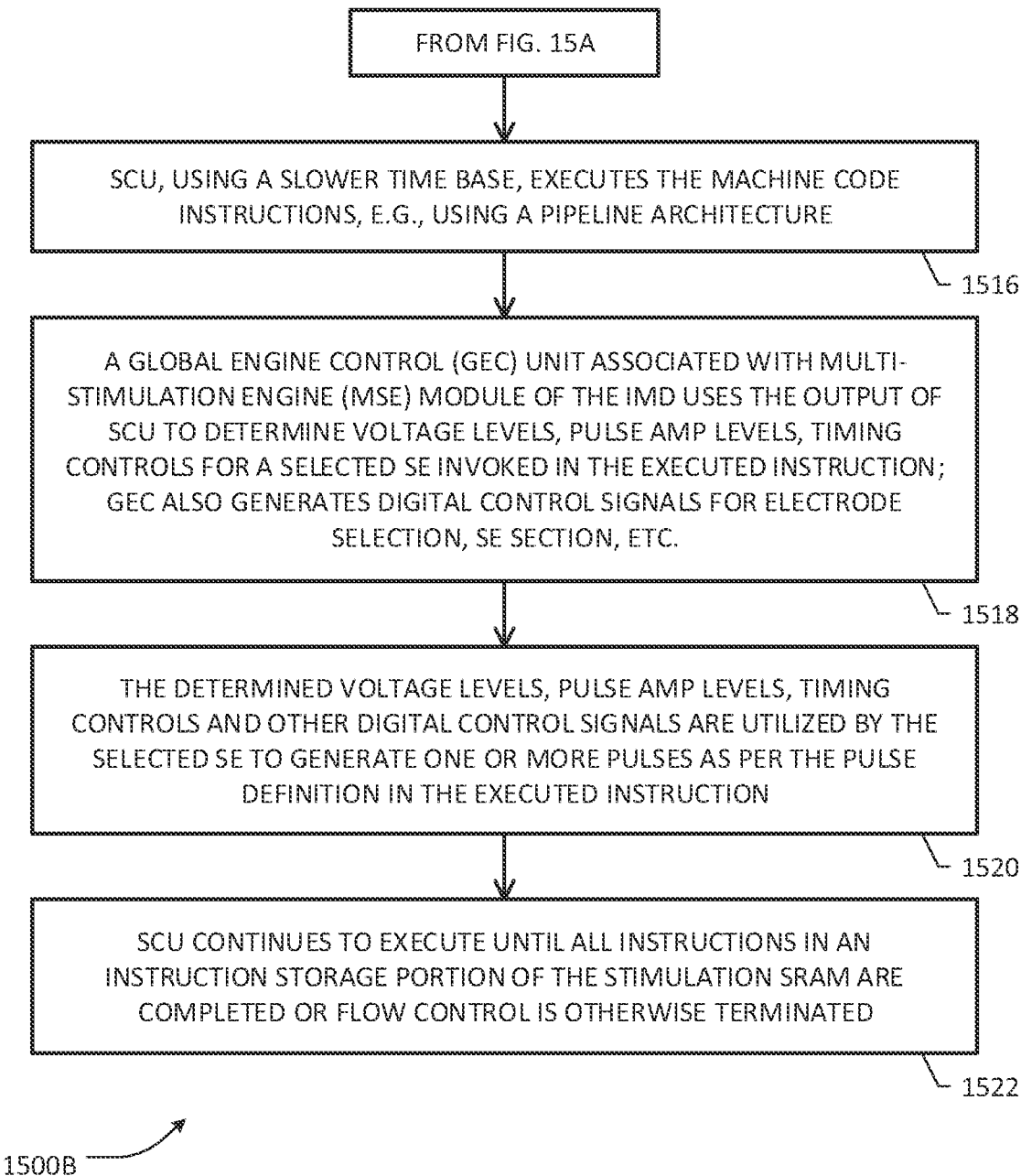

FIGS. 15A and 15B depict a flowchart of blocks, steps and/or acts that may be (re)combined in one or more arrangements, e.g., other flowcharts, for facilitating a stimulation therapy method using a custom ALLIS architecture of an IMD according to some additional and/or alternative embodiments of the present patent disclosure. Process portions 1500A (shown in FIG. 15A) and 1500B (shown in FIG. 15B) form an example process 1500 in one arrangement, which may commence with selection of a therapy program (TP) made by a clinician or a patient at an external device as set forth at block 1502. At block 1504, TP selection is received by the patient's IMD via suitable M2M communications (e.g., via BLE). At block 1508, program code executing on a main processor (e.g., MCU) of the IMD generates a set of pulse definitions and timing definitions corresponding to the selected TP and stores them in main memory (i.e., as stimulation information corresponding to the TP selection). At block 1510, program code executing on the main MCU generates or otherwise obtains a custom instruction set comprising assembly-language-like instructions (ALLI) according to the selected TP. In one embodiment, a compiler may be executed to generate the custom instruction set corresponding to the TP selection. At block 1510, an "assembler" (e.g., executed by or on the MCU) assembles ALLI into binary/machine code stored in main memory or another storage area (e.g., operating as a stimulation SRAM portion). In one arrangement, the main processor may instruct a secondary processor (e.g., SCU) that ALLI and stimulation information are available for execution (e.g., with a starting location pointer in memory), as set forth at block 1512. At block 1514, both stimulation information and machine code instructions may be provided to a cache memory for execution by the SCU. At block 1516, the SCU executes the machine code instructions, e.g., using a pipeline architecture, using a slower time base. At block 1518, a global engine control (GEC) unit associated with a multi-stimulation engine (MSE) module of the IMD uses the output of the SCU to determine voltage levels, pulse amplitude levels, timing controls and other parameters, etc. for a selected SE invoked in the executed instruction. In one arrangement, the GEC unit also generates one or more digital control signals for electrode selection, SE section, discharge operations, and the like. At block 1520, the determined voltage levels, pulse amp levels, timing controls and other digital control signals are utilized by the selected SE to generate one or more pulses as per the pulse definition in the executed instruction. At block 1522, the SCU may continue to execute the stimulation code until all instructions in an instruction storage portion of the stimulation SRAM are completed or the SCU is otherwise instructed to terminate program execution.

Figure 16:
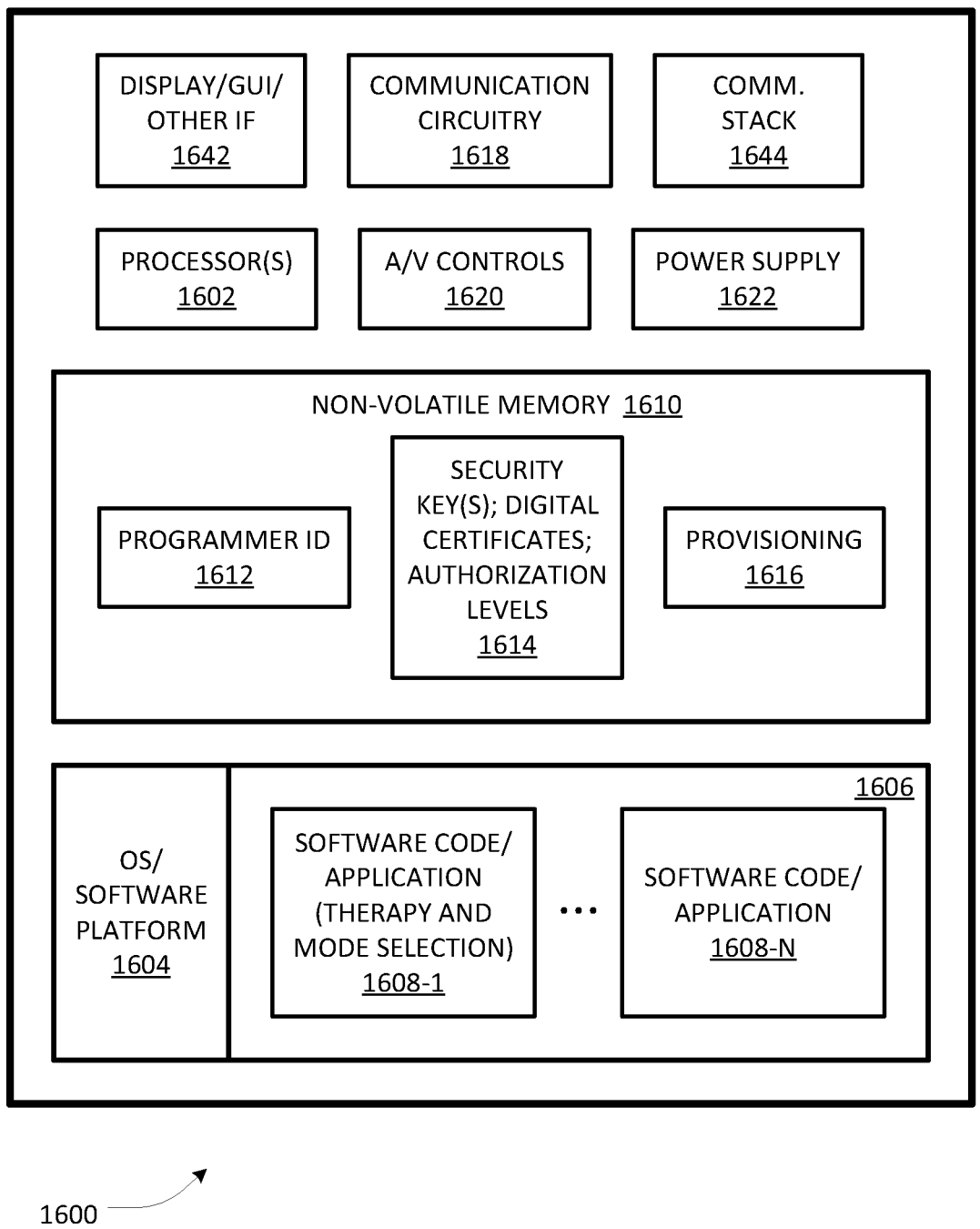
FIG. 16 depicts a block diagram of an external device for purposes of an example embodiment of the present patent disclosure.

FIG. 16 depicts a block diagram of an external device for purposes of an example embodiment of the present patent disclosure that may be configured with an application program operative to execute therapy program selection, test mode functionality, or both, with respect to an IMD. Depending on configuration and/or modality, example external device 1600 may be representative of a clinician programmer device, a patient controller device, a delegated device operated by an agent of a patient or a clinician having subordinate levels of privilege authorization with respect to a therapy/test application, as previously noted. Further, external device 1600 may be a COTS device or non-COTS device as previously noted. Still further, external device 1600 may be a device that is controlled and managed in a centralized enterprise device management system (EDMS), also referred to as a mobile/medical device management system (MDMS), which may be associated with the manufacturer of the IMDs and associated therapy application components in some embodiments (e.g., as an intranet implementation, an extranet implementation, or internet-based cloud implementation, etc.), in order to ensure that only appropriately managed/provisioned devices and users are allowed to engage in communications with IMDs with respect to testing the devices and/or providing therapy to patients using approved therapy applications. Additionally, alternatively and/or optionally, external device 1600 may be a device that is not controlled and managed in such a device management system. Accordingly, it will be realized that external device 1600 may comprise a device that may be configured in a variety of ways depending on how its functional modality is implemented in a particular deployment. Regardless of the myriad combinations, an example embodiment of external device 1600 may be configured to provide a suitable interface to a user upon establishing a communication link with an IMD for selecting a therapy program to provide therapy to a patient via the IMD or launching a test program for testing the components of an IMD.

Example external device 1600 may include one or more processors 1602, communication circuitry 1618 and one or more memory modules 1610, operative in association with one or more OS platforms 1604 and one or more software applications or "apps" 1608-1 to 1608-K depending on configuration, cumulatively referred to as software environment 1606, and any other hardware/software/firmware modules, which may be powered by a power supply 1622, e.g., battery. Example software environment 1606 and/or memory 1610 may include one or more persistent memory modules comprising program code or instructions for controlling overall operations of the device, inter alia. Example OS platforms may include embedded real-time OS systems, and may be selected from, without limitation, iOS, Android, Chrome OS, Blackberry OS, Fire OS, Ubuntu, Sailfish OS, Windows, Kai OS, eCos, LynxOS, QNX, RTLinux, Symbian OS, VxWorks, Windows CE, MontaVista Linux, and the like. In some embodiments, at least a portion of the software applications may include code or program instructions operative as a medical application having therapy and/or test modes, e.g., application 1608-1, which may be configured to interoperate with program code stored in memory 1610 to execute various operations relative to device registration, mode selection, test programming, therapy programming, security applications, and provisioning, etc., as part of a device controller application.

In some embodiments of external device 1600, memory modules 1610 may include a non-volatile storage area or module configured to store relevant patient data, therapy settings, therapy selections, and the like. Memory modules 1610 may further include a secure storage area 1612 to store a device identifier (e.g., a serial number) of device 1600 used during therapy sessions (e.g., local therapy programming or remote therapy programming). Also, memory modules 1610 may include a secure storage area 1614 for storing security credential information, e.g., one or more cryptographic keys or key pairs, signed digital certificates, etc., having various levels of authorization, which may be associated with users (e.g., clinicians, patients, respective agents, authorized field technicians and the like), certificates of trusted provisioning entities, etc. In some arrangements, such security credential information may be specifically operative in association with approved/provisioned software applications, e.g., therapy/test application 1608-1, which may be obtained during provisioning. A non-volatile storage area 1616 may also be provided for storing provisioning data, validation data, settings data, metadata etc. Communication circuitry 1618 may include appropriate hardware, software and interfaces to facilitate wireless and/or wireline communications, e.g., inductive communications, wireless telemetry or M2M communications, etc. to effectuate IMD communications, as well as networked communications with cellular telephony networks, local area networks (LANs), wide area networks (WANs), packet-switched data networks, etc., based on a variety of access technologies and communication protocols, which may be controlled by therapy application program 1608-1 depending on implementation.

For example, application 1608-1 may include code or program instructions configured to effectuate wireless telemetry and authentication with an IMD or wearable medical device using a suitable M2M communication protocol stack which may be mediated via virtual/digital assistant technologies in some arrangements. By way of illustration, one or more bi-directional communication links with a device may be effectuated via a wireless personal area network (WPAN) using a standard wireless protocol such as Bluetooth Low Energy (BLE), Bluetooth, Wireless USB, Zigbee, Near-Field Communications (NFC), WiFi (e.g., IEEE 802.11 suite of protocols), Infrared Wireless, and the like. In some arrangements, bi-directional communication links may also be established using magnetic induction techniques rather than radio waves, e.g., via an induction wireless mechanism. Alternatively and/or additionally, communication links may be effectuated in accordance with certain healthcare-specific communications services including, Medical Implant Communication Service (MICS), Wireless Medical Telemetry Service (MTS), Medical Device Radiocommunications Service (MDRS), Medical Data Service (MDS), etc. Accordingly, regardless of which type(s) of communication technology being used, external device 1600 may be provided with one or more communication protocol stacks 1644 operative with hardware, software and firmware (e.g., forming suitable communication circuitry including transceiver circuitry and antenna circuitry where necessary, which may be collectively exemplified as communication circuitry 1618 as previously noted) for effectuating appropriate short-range and long-range communication links for purposes of some example embodiments herein. In still further embodiments, such short-range and/or long-range communication links may be mediated via home/office-based smart virtual/digital assistant technologies.

External device 1600 may also include appropriate audio/video controls 1620 as well as suitable display(s) (e.g., touch screen), camera(s), microphone, and other user interfaces (e.g., GUIs) 1642, which may be utilized for purposes of some example embodiments of the present disclosure, e.g., facilitating user input, initiating IMD/network communications, mode selection, therapy selection, etc., which may depend on the aspect(s) of a particular therapy application being implemented.

Based on the foregoing, skilled artisans will appreciate that embodiments herein provide a custom ISA scheme that advantageously facilitates stimulation therapy using one or more SEs that may be individually controlled and configured. Example embodiments may therefore be configured to improve compatibility and ease of programming/control of therapy delivery in the context of emerging complex stimulation programs where it would otherwise become increasingly difficult to predict and to avoid therapy collisions, which typically occur in multi-frequency, multi-lead applications such as, e.g., dual brain hemisphere DBS therapies. Accordingly, example embodiments of the present disclosure may be practiced in a variety of therapy applications including but not limited to SCS therapy, DBS therapy, DRG therapy, cochlear stimulation therapy, drug delivery therapy, cardiac pacemaker therapy, cardioverter-defibrillator therapy, cardiac rhythm management (CRM) therapy, an electrophysiology (EP) mapping and radio frequency (RF) ablation therapy, electroconvulsive therapy (ECT), repetitive transcranial magnetic stimulation (rTMS) therapy, and vagal nerve stimulation (VNS) therapy, and the like.

It should be further appreciated that whereas novel waveform generation for neuromodulation is in its infancy at this point, and the current state of the art implementations require high computation power with limited flexibility as to what they can output because of the involvement of a faster MCU that is typically required in today's device implementations, embodiments disclosed herein advantageously overcome such deficiencies. By providing a secondary processing module that runs at a slower clock for servicing stimulation instructions at a machine code level, an example therapy system is not only optimized for lower power consumption (thereby increasing the battery life) but may also be configured to generate newer pulse definitions/attributes "on the fly", e.g., by performing ALU operations on a register level that can create newer definitions without the involvement of power hungry main MCU operations.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, some example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or nonvolatile memories such as, e.g., random access memory (RAM), electrically erasable/programmable read-only memories (EEPROMs) or UV-EPROMS, one-time programmable (OTP) memories, Flash memories, static RAM (SRAM), etc.

Various types of switching circuit blocks as well as associated control logic signals as set forth in the example embodiments may be implemented in myriad ways using a broad range of electronic devices known in the electrical arts, e.g., including but not limited to bipolar junction transistors (BJTs), metal oxide semiconductor field effect transistors (MOSFETS), junction gate FETs (JFETs), n-channel MOSFET (NMOS) devices, p-channel MOSFET (PMOS) devices, depletion-mode or enhancement-mode devices, diodes, and the like, as well as any digital logic gates built therefrom. It will be further understood that the sizing (e.g., channel width and length) and biasing of the switching devices is highly configurable, e.g., depending on whether anodic current stimulation or cathodic stimulation current is being programmed (i.e., whether the electrodes of a lead system are configured to operate as current sink terminals or cathodes, or as current source terminals or anodes) as well as how much current is to be carried for each electrode set (i.e., granularity and distribution of the currents drawn from respective loads).

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import are recited or described, such a phrase should be understood to mean "only A, only B, or both A and B." Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A method of operating an implantable medical device (IMD) for providing stimulation therapy to a patient, the IMD including one or more stimulation engines (SEs) operatively coupled to at least one implantable lead having a plurality of electrodes positioned proximate to a tissue of the patient, the method comprising:

generating, by a first processor of the IMD operative with a first clock frequency, a set of pulse definitions and a set of timing definitions corresponding to a therapy program selection received from an external device responsive to a user input thereat;

storing the respective sets of pulse definitions and timing definitions in a storage area;

generating, by the first processor, a sequence of assembly-language like (ALL) instructions for execution by a second processor of the IMD operative with a second clock frequency that is lower than the first clock frequency, the second processor configured to control the one or more SEs for generating one or more pulse waveforms; and executing at least a portion of the ALL instructions by the second processor for causing the one or more SEs to generate a particular sequence of therapy pulses according to the therapy program selection based on respective combinations of pulse definitions and timing definitions applied over a time base in accordance with the executed ALL instructions.

2. The method as recited in claim 1, wherein the at least a portion of the ALL instructions are executed by the second processor using instruction pipelining.

3. The method as recited in claim 1, wherein the time base is derived from the second clock frequency of the second processor, the time base comprising a clock signal, and further wherein a verification is performed at each clock edge of the clock signal to determine whether there are any pending instructions to be executed.

4. The method as recited in claim 1, wherein the therapy program selection comprises selecting a therapy program having a tonic stimulation pattern, a burst stimulation pattern, a high-frequency stimulation pattern, a sub-paresthesia stimulation pattern, a non-paresthesia stimulation pattern, a biphasic pulse stimulation pattern or a monophasic pulse stimulation pattern.

5. The method as recited in claim 1, wherein the therapy program selection comprises selecting a therapy program for effectuating a spinal cord stimulation (SCS) therapy, a neuromuscular stimulation therapy, a dorsal root ganglion (DRG) stimulation therapy, a deep brain stimulation (DBS) therapy, a cochlear stimulation therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, or a vagal nerve stimulation (VNS) therapy.

6. The method as recited in claim 1, wherein the therapy program selection is received from a clinician programmer device operating as the external device responsive to a clinician input.

7. The method as recited in claim 1, wherein the therapy program selection is received from a patient controller device operating as the external device responsive to an input by the patient.

* * * * *